(12) United States Patent
Chenvainu et al.

(10) Patent No.: US 8,317,424 B2
(45) Date of Patent: *Nov. 27, 2012

(54) ORAL CARE DEVICE

(75) Inventors: Alexander T. Chenvainu, Sudbury, MA (US); Thomas A. Christman, Lexington, MA (US); Jeremy Ducharme, Reading, MA (US); Mark E. Farrell, Medfield, MA (US)

(73) Assignee: The Gillette Company, Boston, MA (US)

(*) Notice: Subject to any disclaimer, the term of this patent is extended or adjusted under 35 U.S.C. 154(b) by 1356 days.

This patent is subject to a terminal disclaimer.

(21) Appl. No.: 10/861,285

(22) Filed: Jun. 3, 2004

(65) Prior Publication Data
US 2005/0272002 A1 Dec. 8, 2005

(51) Int. Cl.
*B43K 5/02* (2006.01)
*A61C 17/00* (2006.01)
*A61C 5/04* (2006.01)

(52) U.S. Cl. .......................... 401/188 R; 453/80; 453/89

(58) Field of Classification Search ............... 433/80–85, 433/126, 89; 601/162–165; 15/22.1–22.2; 251/149, 149.1–149.7; 137/614, 614.02, 137/164–164.7; 417/412, 474, 478, 479, 417/477.1, 477.3, 477.4, 477.7, 477.12; 401/152, 401/155, 156, 158, 160, 163–168, 188 R, 401/270, 278, 183–186; 604/131, 151, 154–155; 132/308, 311, 112–116; 222/333, 325, 327
See application file for complete search history.

(56) References Cited

U.S. PATENT DOCUMENTS

| | | | |
|---|---|---|---|
| 2,709,546 A | 5/1955 | Shore | |
| 3,536,065 A | 10/1970 | Moret | |
| 3,910,706 A | 10/1975 | Del Bon | 401/134 |
| 4,049,354 A * | 9/1977 | O'Rourke | 401/134 |
| 4,155,663 A | 5/1979 | Cerquozzi | 401/135 |
| 4,178,975 A | 12/1979 | Crespi | 141/362 |
| 4,583,563 A | 4/1986 | Turner | 132/84 |
| 4,770,613 A * | 9/1988 | Hoover et al. | 417/411 |
| 5,199,604 A * | 4/1993 | Palmer et al. | 222/25 |
| 5,208,933 A | 5/1993 | Lustig et al. | 15/22.1 |
| 5,301,381 A | 4/1994 | Klupt | 15/22.1 |
| 5,321,866 A | 6/1994 | Klupt | 15/22.1 |

(Continued)

FOREIGN PATENT DOCUMENTS

CA 1151 821 8/1983

(Continued)

OTHER PUBLICATIONS

U.S. Appl. No. 11/635,697, filed Dec. 7, 2006, Burrowes.

(Continued)

*Primary Examiner* — Yogesh Patel
(74) *Attorney, Agent, or Firm* — Julia A. Glazer; Carrie M. Benjamin; Vladimir Vitenberg

(57) ABSTRACT

Oral care devices are provided that include a first component and a second component removably engaged with the first component; the first and second components having a respective fluid passageway extending therethrough, the respective passageways capable of fluid communication while the first and second components are engaged; and at least one of the first and second components including a sealing member constructed to allow fluid communication between the first and second passageways when the first and second passageways are engaged and to close the associated passageway when the first and second components are disengaged. Oral care devices are also provided that include a replaceable and refillable cartridge.

13 Claims, 44 Drawing Sheets

U.S. PATENT DOCUMENTS

| | | | | |
|---|---|---|---|---|
| 5,343,904 A * | 9/1994 | Kaeser | | 141/20 |
| 5,346,324 A * | 9/1994 | Kuo | | 401/146 |
| 5,454,896 A | 10/1995 | Harding et al. | | 156/156 |
| 5,494,074 A * | 2/1996 | Ramacier et al. | | 137/614.04 |
| 5,524,312 A | 6/1996 | Tan et al. | | 15/22.1 |
| 5,540,358 A | 7/1996 | Wiles et al. | | 222/107 |
| 5,573,398 A | 11/1996 | Towle et al. | | |
| 5,600,933 A | 2/1997 | Wiles et al. | | 53/133.4 |
| 5,655,906 A * | 8/1997 | Coss et al. | | 433/115 |
| 5,820,373 A | 10/1998 | Okano et al. | | 433/80 |
| 5,860,949 A * | 1/1999 | Chen | | 604/35 |
| 5,909,977 A * | 6/1999 | Kuo | | 401/146 |
| 5,921,692 A | 7/1999 | Weber | | 401/119 |
| 5,974,613 A | 11/1999 | Herzog | | 15/22.1 |
| 6,039,301 A | 3/2000 | Westerhof | | 251/144 |
| 6,161,579 A * | 12/2000 | Vulliet | | 137/614.05 |
| 6,164,967 A | 12/2000 | Sale et al. | | 433/80 |
| 6,179,503 B1 * | 1/2001 | Taghavi-Khanghah | | 401/184 |
| 6,220,772 B1 | 4/2001 | Taylor | | 401/176 |
| 6,241,412 B1 | 6/2001 | Spies et al. | | 401/129 |
| 6,315,483 B1 | 11/2001 | Velliquette | | |
| 6,371,674 B1 | 4/2002 | Lerner | | 401/155 |
| 6,402,410 B1 | 6/2002 | Hall et al. | | 401/146 |
| 6,434,773 B1 | 8/2002 | Kuo | | 15/22.1 |
| 6,574,820 B1 | 6/2003 | DePuydt et al. | | 15/28 |
| 6,575,203 B2 | 6/2003 | Hall et al. | | 141/18 |
| 6,644,878 B2 | 11/2003 | Hall et al. | | 401/146 |
| 6,648,641 B1 | 11/2003 | Viltro et al. | | 433/80 |
| 6,745,998 B2 | 6/2004 | Doyle | | |
| 6,766,824 B2 | 7/2004 | Taylor | | 137/522 |
| 6,808,331 B2 | 10/2004 | Hall | | 401/188 |
| 6,902,337 B1 | 6/2005 | Kuo | | |
| 2002/0108193 A1 | 8/2002 | Gruber | | 15/22.1 |
| 2003/0013063 A1* | 1/2003 | Goldman | | 433/80 |
| 2003/0033680 A1 | 2/2003 | Davies et al. | | 15/22.1 |
| 2003/0037447 A1 | 2/2003 | Gruber et al. | | |
| 2003/0056307 A1 | 3/2003 | Tybinkowski et al. | | 15/29 |
| 2003/0150472 A1 | 8/2003 | Johnson | | 132/311 |
| 2003/0194678 A1 | 10/2003 | Viltro et al. | | |
| 2003/0198503 A1* | 10/2003 | Gordon | | 401/278 |
| 2003/0221270 A1* | 12/2003 | Kuo | | 15/29 |
| 2004/0018475 A1 | 1/2004 | Healey et al. | | 434/298 |
| 2004/0047676 A1 | 3/2004 | Dumler | | |
| 2004/0057773 A1 | 3/2004 | Gray | | 401/277 |
| 2004/0072122 A1 | 4/2004 | Hegemann | | 433/80 |
| 2004/0126331 A1 | 7/2004 | Corcoran et al. | | 424/49 |
| 2004/0131560 A1 | 7/2004 | Corcoran et al. | | |
| 2004/0141799 A1 | 7/2004 | Jackow | | 401/284 |
| 2004/0209222 A1 | 10/2004 | Snyder et al. | | |
| 2005/0004498 A1 | 1/2005 | Klupt | | |
| 2005/0158688 A1 | 7/2005 | Tarr | | 433/125 |
| 2005/0271531 A1 | 12/2005 | Christman et al. | | |
| 2005/0272001 A1 | 12/2005 | Blain et al. | | |
| 2006/0078844 A1 | 4/2006 | Cohen et al. | | |
| 2006/0188454 A1 | 8/2006 | Corcoran et al. | | |
| 2006/0193792 A1 | 8/2006 | Corcoran et al. | | |
| 2006/0240380 A1 | 10/2006 | Chenvainu et al. | | |
| 2007/0017582 A1 | 1/2007 | Chenvainu et al. | | |
| 2007/0254260 A1 | 11/2007 | Alden et al. | | |

FOREIGN PATENT DOCUMENTS

| | | |
|---|---|---|
| DE | 2343421 | 3/1975 |
| DE | 9107226 | 8/1991 |
| DE | 298 16 089 U1 | 1/1999 |
| GB | 2085717 A | 5/1982 |
| JP | 9215524 A | 8/1997 |
| WO | WO 82/00576 | 3/1982 |
| WO | WO 00/41645 | 7/2000 |
| WO | WO 00/74592 A1 | 12/2000 |
| WO | WO 02/41801 A1 | 5/2002 |
| WO | WO 02/41802 A1 | 5/2002 |
| WO | WO 02/087464 A1 | 11/2002 |
| WO | WO 2004/054403 A1 | 7/2004 |
| WO | WO 2004/056287 A1 | 7/2004 |
| WO | WO 2004/060259 A2 | 7/2004 |
| WO | WO 2005/058185 A1 | 6/2005 |

OTHER PUBLICATIONS

International Search Report received in connection with PCT/US2005/017715, mailed on Oct. 11, 2005, 3 pages.

US Patent and Trademark Office Communication for U.S. Appl. No. 10/861,086, mailed on Dec. 10, 2007, 22 pages.

US Patent and Trademark Office Communication for U.S. Appl. No. 11/185,480, mailed on Dec. 28, 2007, 13 pages.

\* cited by examiner

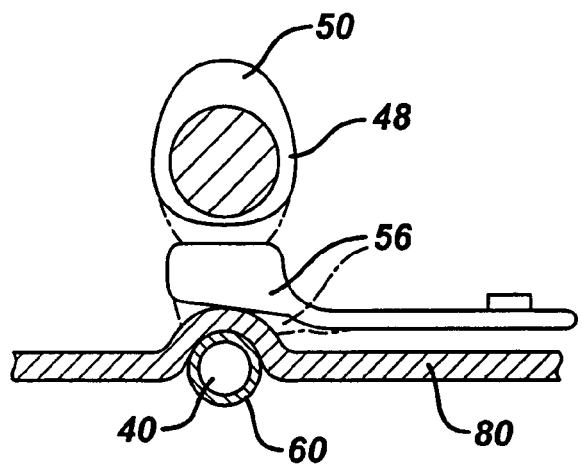
FIG. 8
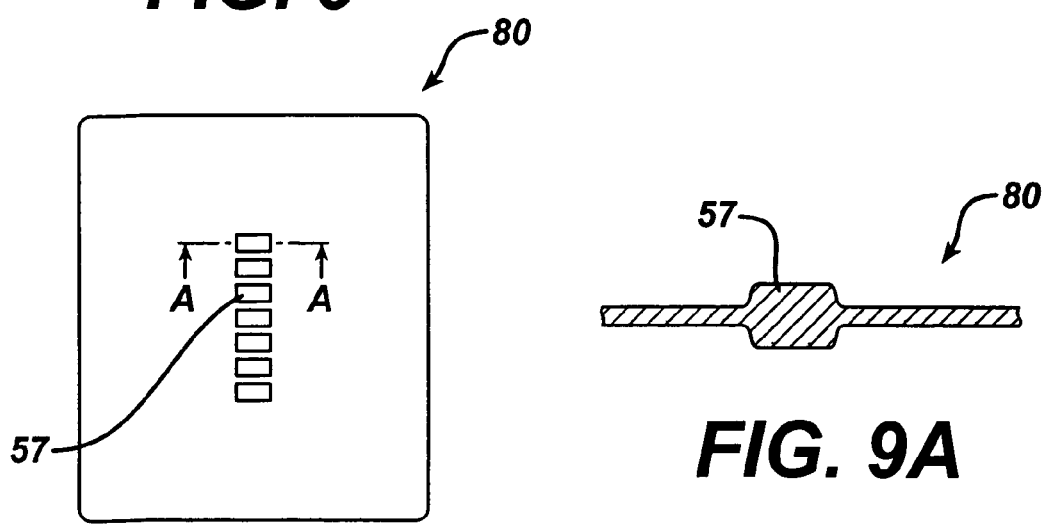
FIG. 9
FIG. 9A

FIG. 18A FIG. 18B
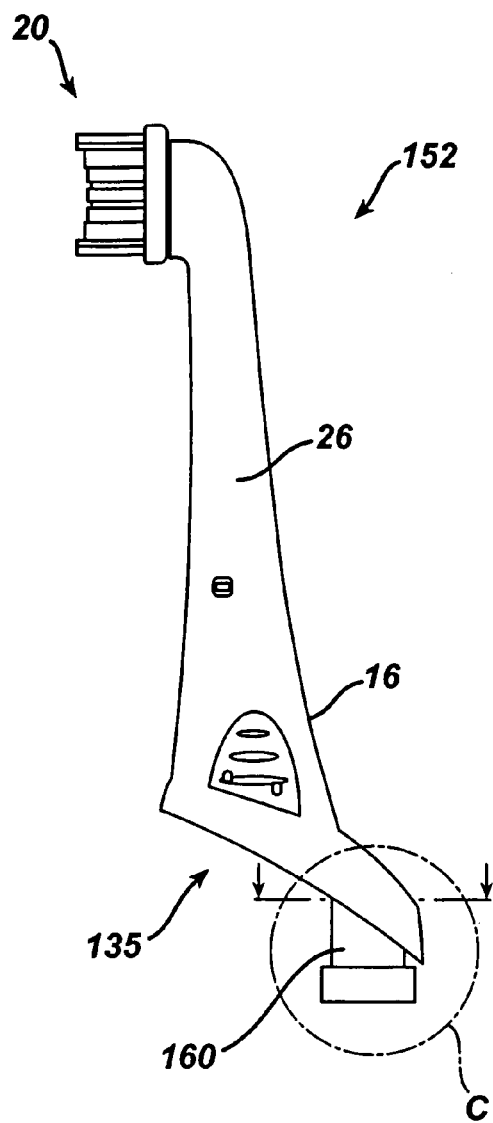
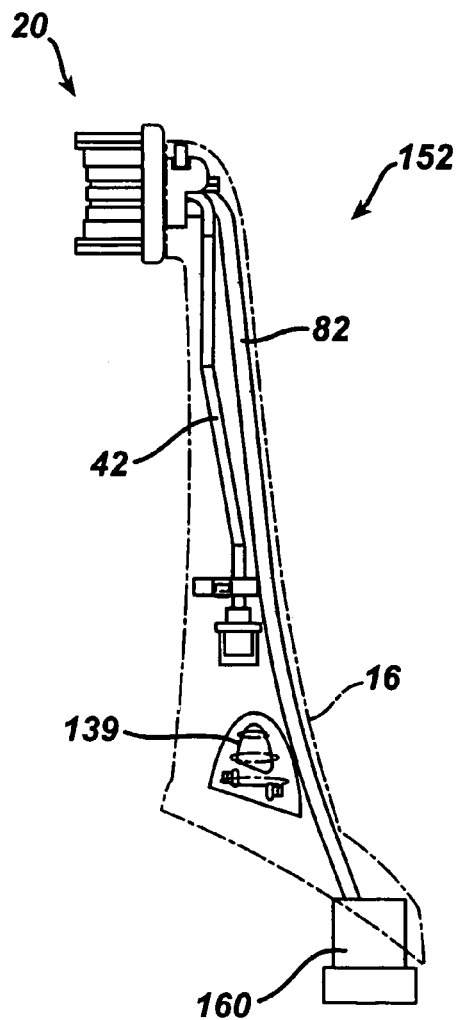

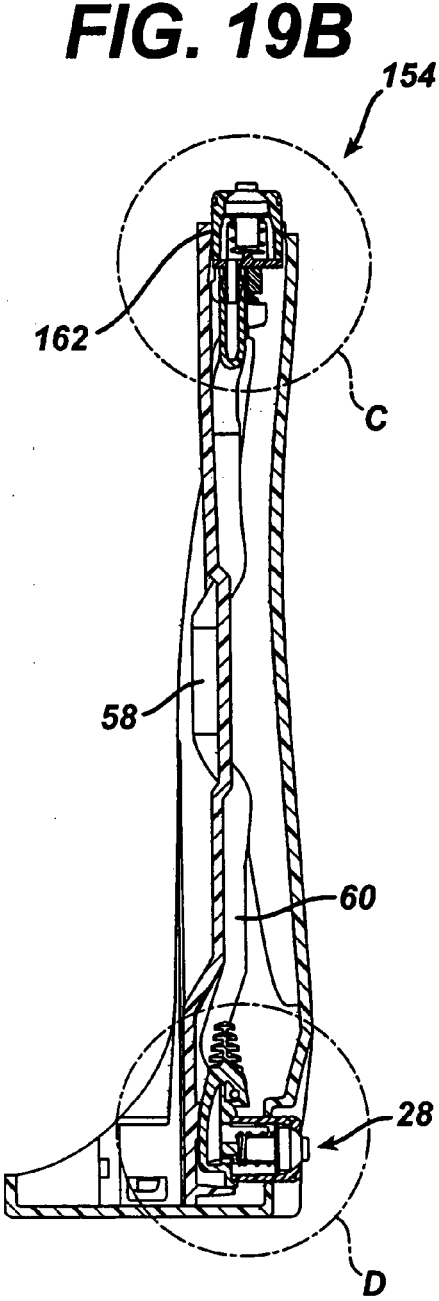

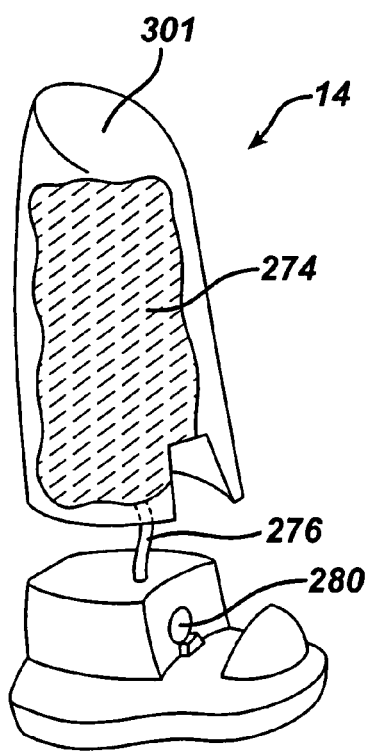 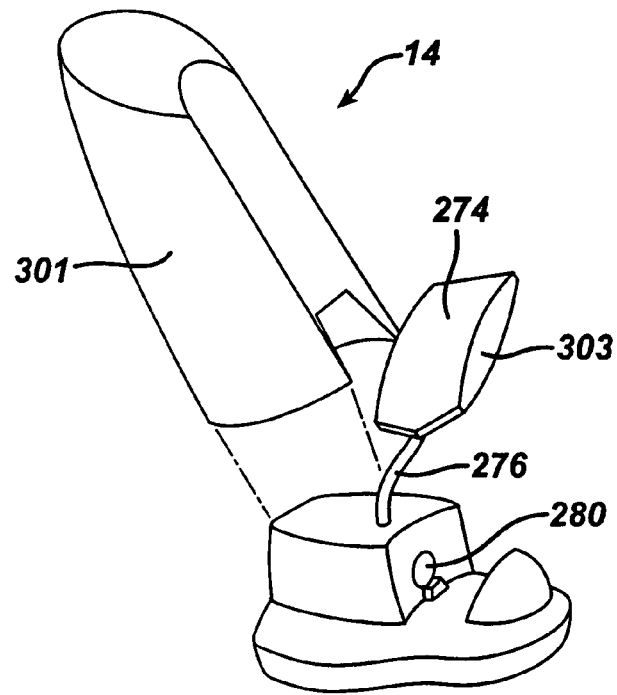
FIG. 24　　　FIG. 25

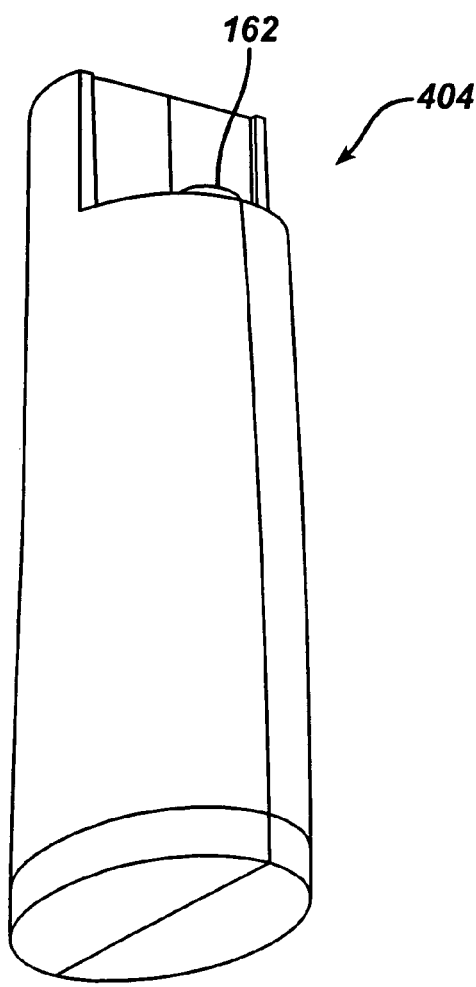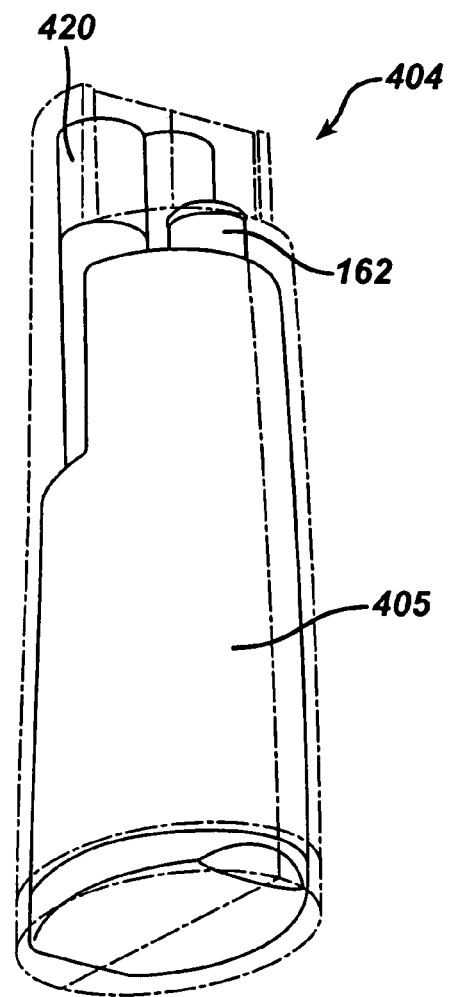
FIG. 30A   FIG. 30B

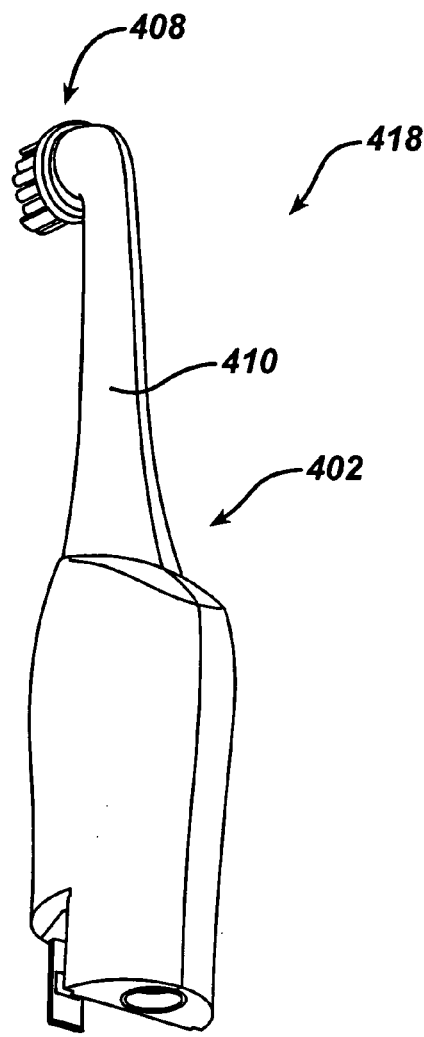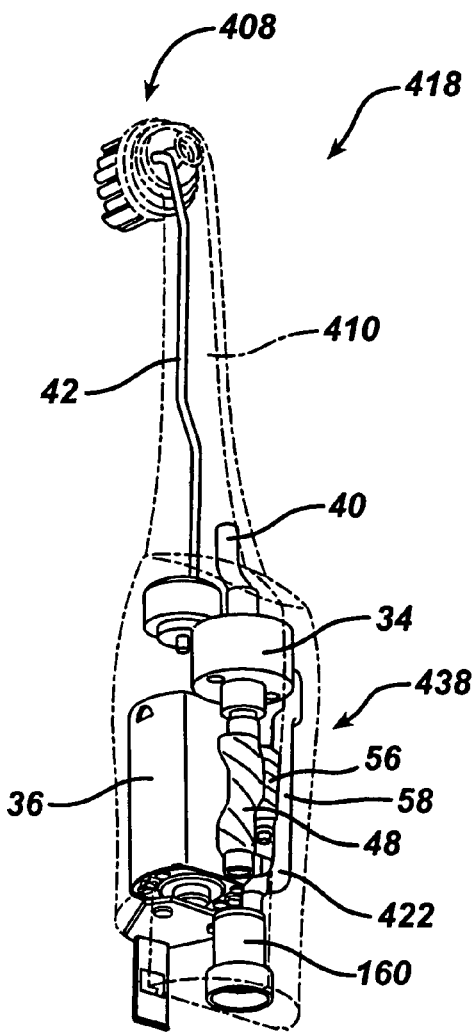
FIG. 31A  FIG. 31B

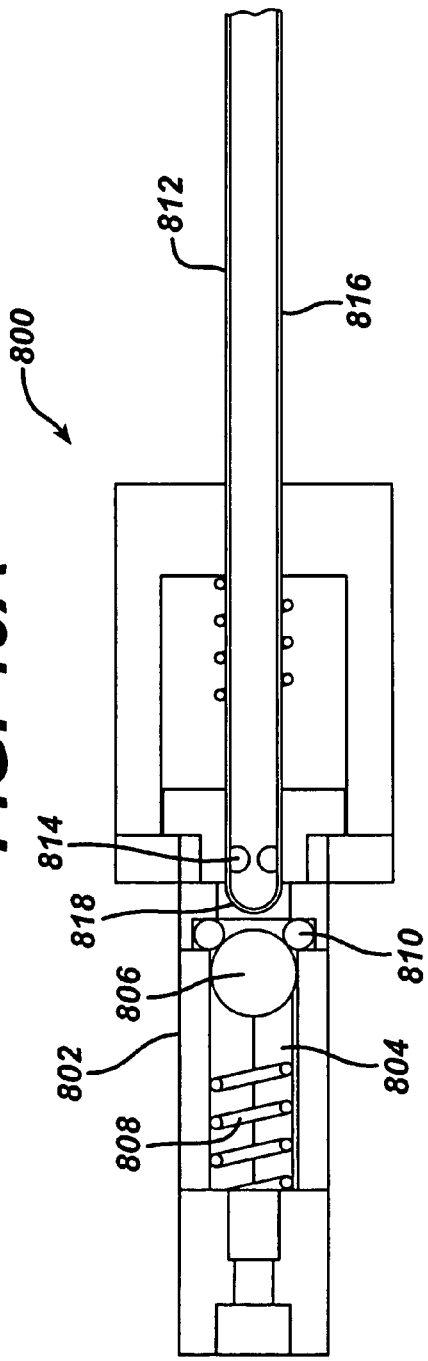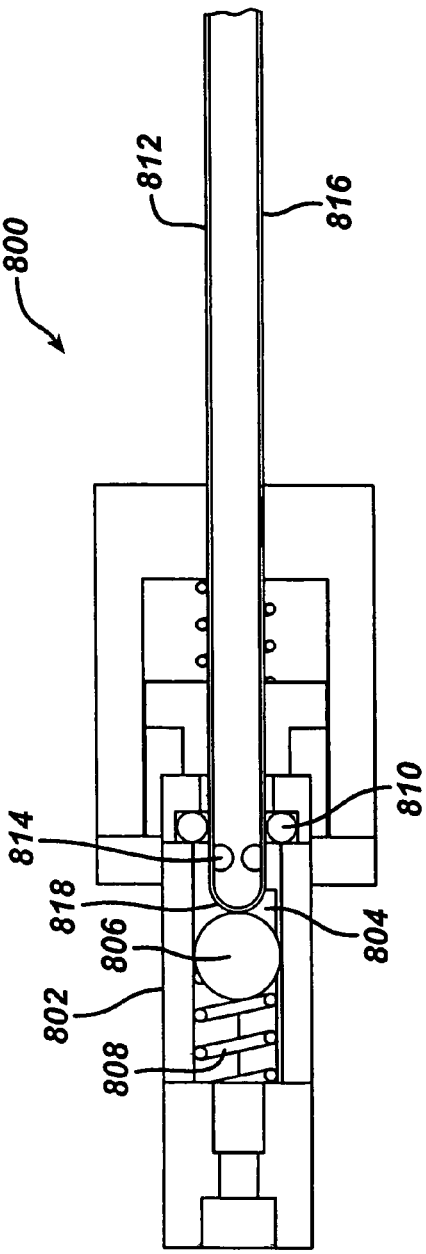
FIG. 40A
FIG. 40B

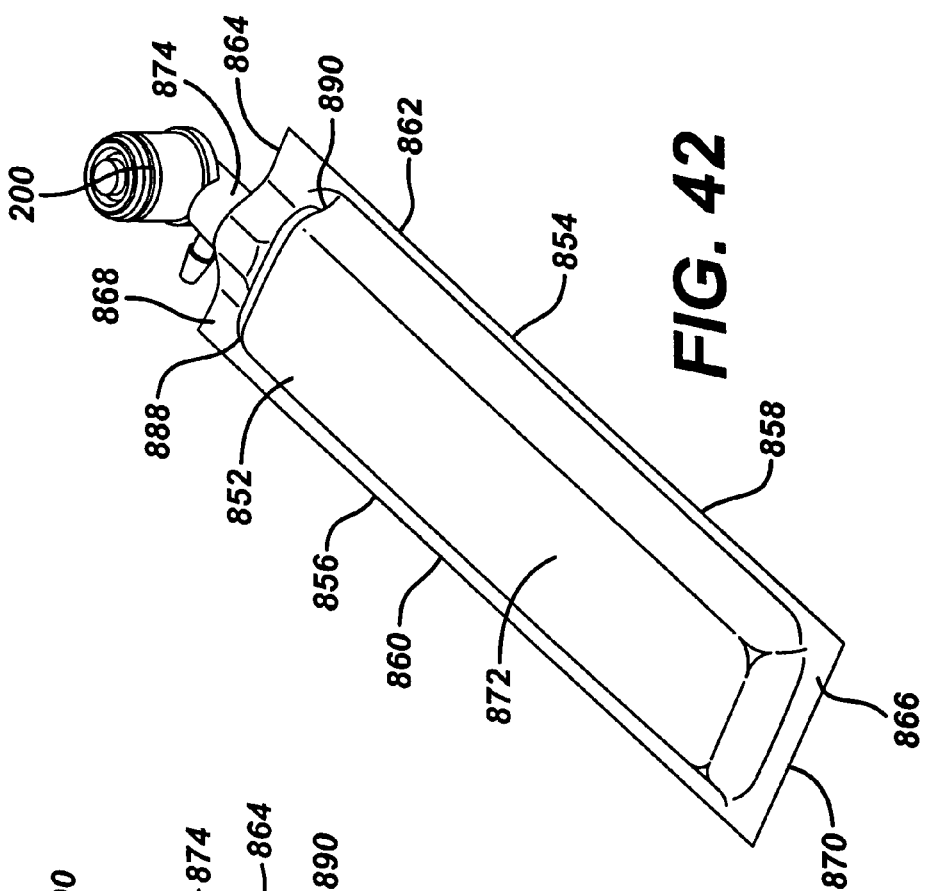
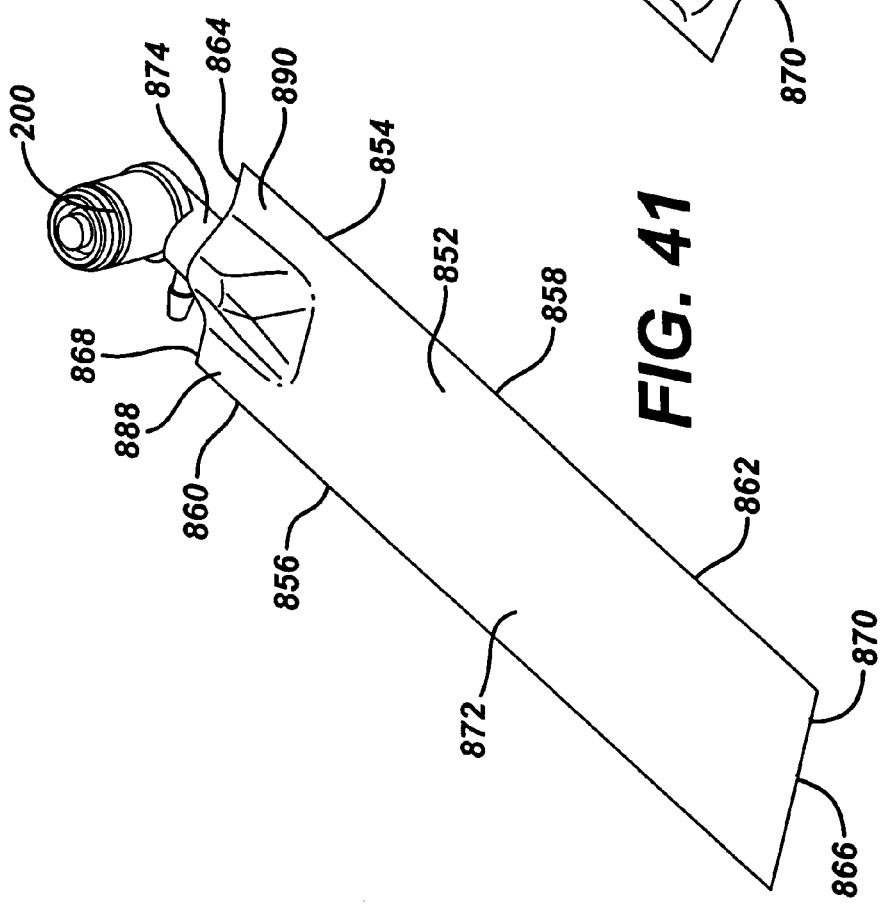

ORAL CARE DEVICE

TECHNICAL FIELD

This invention relates to oral care systems and methods of their use.

BACKGROUND

Conventional toothbrushes, having tufts of bristles mounted on a head, are generally effective at removing plaque from the flat surfaces of teeth and the areas between teeth and along the gumline that can be accessed by the bristles. Typically, a consumer manually squeezes a globule of paste from a tube onto the bristles of the conventional brush prior to placing the brush in their mouth. After paste is deposited on the bristles, the brush is placed in their mouth and brushing commences. As a further development on conventional toothbrushes, U.S. Serial No. 2002/0108193 proposes a sonic power toothbrush that is capable of dispensing additives at the head of the brush. The head can vibrate relative to the body of the brush due to sonic frequency vibrations that are transmitted to the brush head.

SUMMARY

In one aspect, the invention features an oral care device that includes a first component and a second component removably engaged with the first component; the first and second components having a respective fluid passageway extending therethrough, the respective passageways capable of fluid communication while the first and second components are engaged; and at least one of the first and second components including a sealing member constructed to allow fluid communication between the first and second passageways when the first and second passageways are engaged and to close the associated passageway when the first and second components are disengaged.

Some implementations may include one or more of the following features. The passageways may be connected at an air-tight connection to prevent outside air from entering the passageways at the connection when the first and second components are engaged. In some embodiments, only one of the first and second components includes a sealing member that closes the respective passageway when the first and second components are disengaged. Alternatively, each of the first and second components may include a sealing member that closes the respective passageway when the first and second components are disengaged. Each sealing member may be biased, e.g., by a spring, toward a portion of the respective passageway of reduced dimension to close the respective passageways when the first and second components are disengaged. The sealing members may be configured to deflect each other when the first and second components are engaged to open the passageways and allow fluid communication between the passageways. The sealing members and respective passageways may be configured to restrict the motion of the sealing members to inhibit the sealing members from closing the respective passageways during use when the first and second components are engaged. The sealing member may be disposed at an end of the associated passageway for closing the associated passageway at the end. The first component may include a head portion sized to fit within a user's mouth. The oral care device may further include a third component releasably connected to at least one of the first and second components. The third component may include a drive mechanism, e.g., an electric motor. When the sealing member closes the respective passageway when the first and second components are disengaged, the sealing member may form a fluid-tight seal and/or an air-tight seal.

In another aspect, the invention features an oral care device that includes a head component including a head portion sized to fit within a user's mouth and a first fluid passageway for directing fluid to an outlet at the head portion; and a replaceable and refillable cartridge releasably connected to the head component, the cartridge comprising a second fluid passageway in fluid communication with the first fluid passageway.

Some implementations may include one or more of the following features. The cartridge may include an inlet for refilling the cartridge and an outlet connected to the first fluid passageway, the inlet and the outlet being in communication with the second fluid passageway. The cartridge may be configured to be refillable while connected to the head component. The oral care device may also include a valve in fluid communication with the respective fluid passageways when the head component and cartridge component are connected. The valve may be configured to close one of the respective fluid passageways when the head component and cartridge components are separated.

The invention also features methods of using oral care devices. For example, in one aspect the invention features a method of replacing a cartridge component of an oral care device, including (a) disconnecting a connection between a reservoir and a head component, the connection capable of providing communication between associated passageways when the head and cartridge components are engaged; while (b) sealing at least one of the passageways.

The details of one or more embodiments of the invention are set forth in the accompanying drawings and the description below. Other features and advantages of the invention will be apparent from the description and drawings, and from the claims.

DESCRIPTION OF DRAWINGS

FIG. 8 is a side view of elements of a pumping assembly including a flexible membrane.

FIGS. 9 and 9A illustrates another flexible membrane embodiment.

FIGS. 18A and 18B are side views of an embodiment of a separable component forming part of the oral care device of FIG. 2A.

FIGS. 19A and 19B are side and sectional views, respectively, of an embodiment of a separable cartridge component forming part of the oral care device of FIG. 2A.

FIG. 24 illustrates a docking station embodiment.

FIG. 25 illustrates another docking station embodiment.

FIGS. 30A and 30B are, respectively, side perspective and transparent views of a separable component forming part of the oral care device of FIG. 29.

FIGS. 31A and 31B are, respectively, side perspective and transparent views of a separable component forming part of the oral care device of FIG. 29.

FIGS. 40A and 40B are section views of an alternative valve assembly embodiment.

FIGS. 41, 42 and 44 are perspective views of different fluid reservoir embodiments

DETAILED DESCRIPTION

Figure 1:
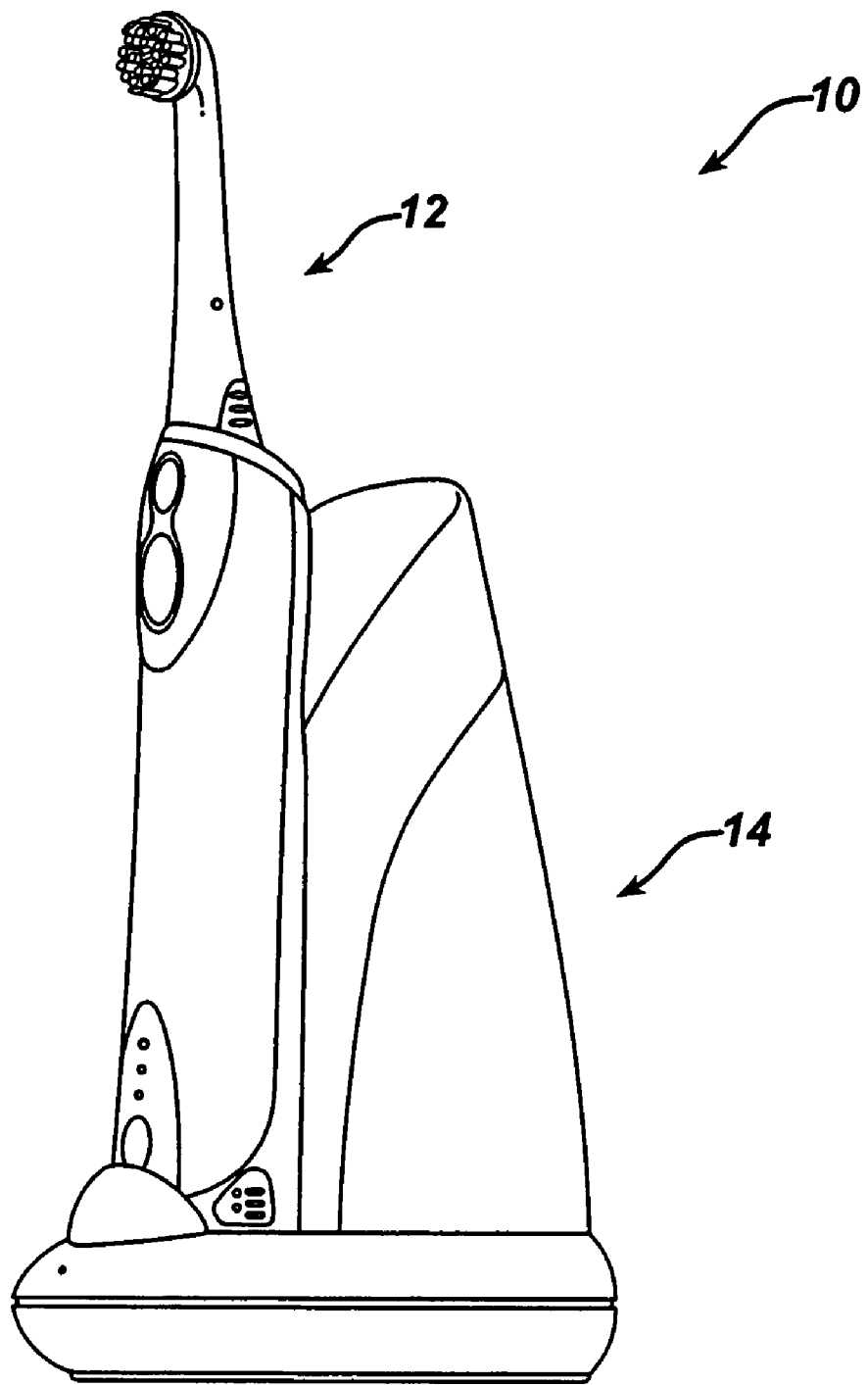
FIG. 1 is a side perspective view of an embodiment of an oral care system.

Referring to FIG. 1, an embodiment of an oral care system 10 is shown that includes an oral care device 12, in this case a toothbrush, and a docking station 14 that holds the oral care device 12 in an upright position within a receiving portion of the docking station. As will be described in much greater detail below, oral care device 12 is a power toothbrush having a motorized head and is designed to discharge a fluid, such as a dentifrice or mouthwash or a combination of various fluids, during the brushing cycle. The docking station 14 is designed to recharge batteries that are located within the oral care device, and to refill the oral care device with the fluid(s).

Figure 2A:
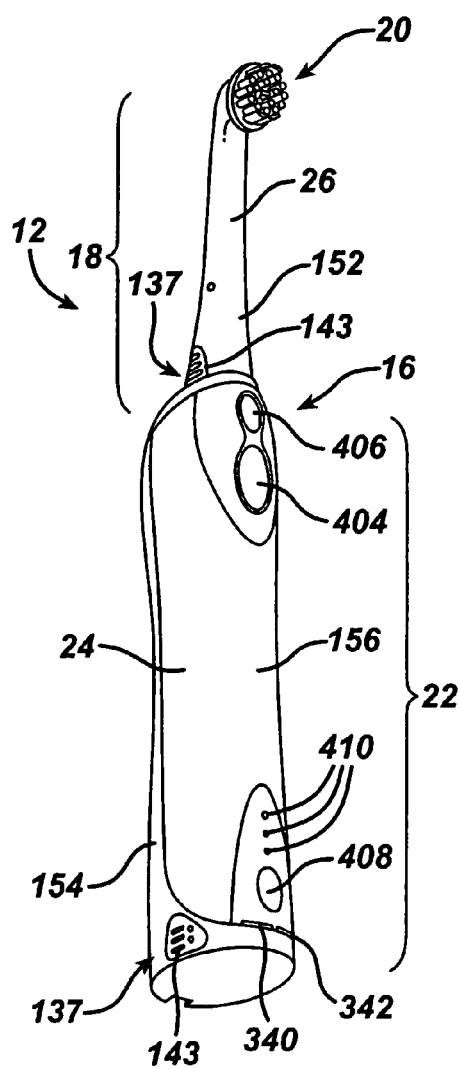
FIG. 2A is a front perspective view of an embodiment of an oral care device.
Figure 2B:
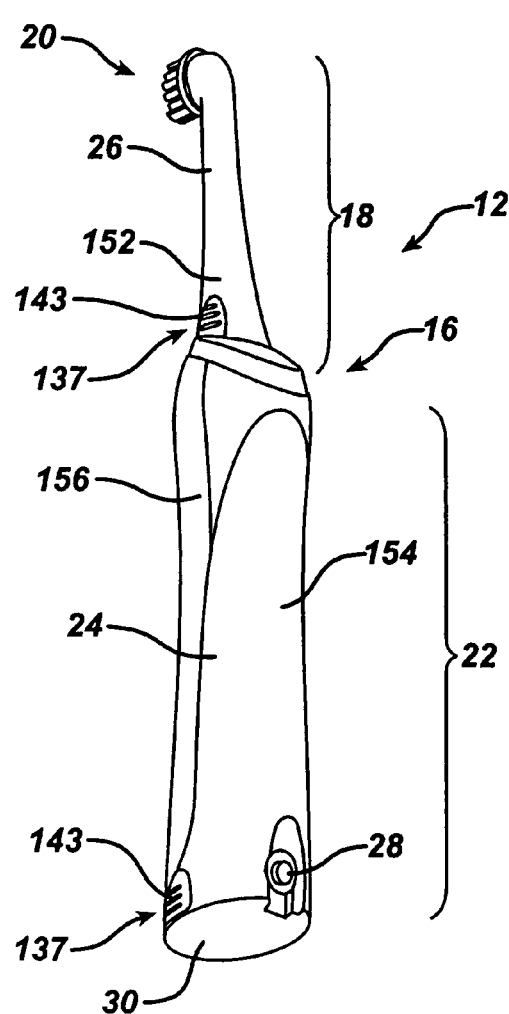
FIG. 2B is a rear perspective view of the oral care device of FIG. 2A.
Figure 19C:
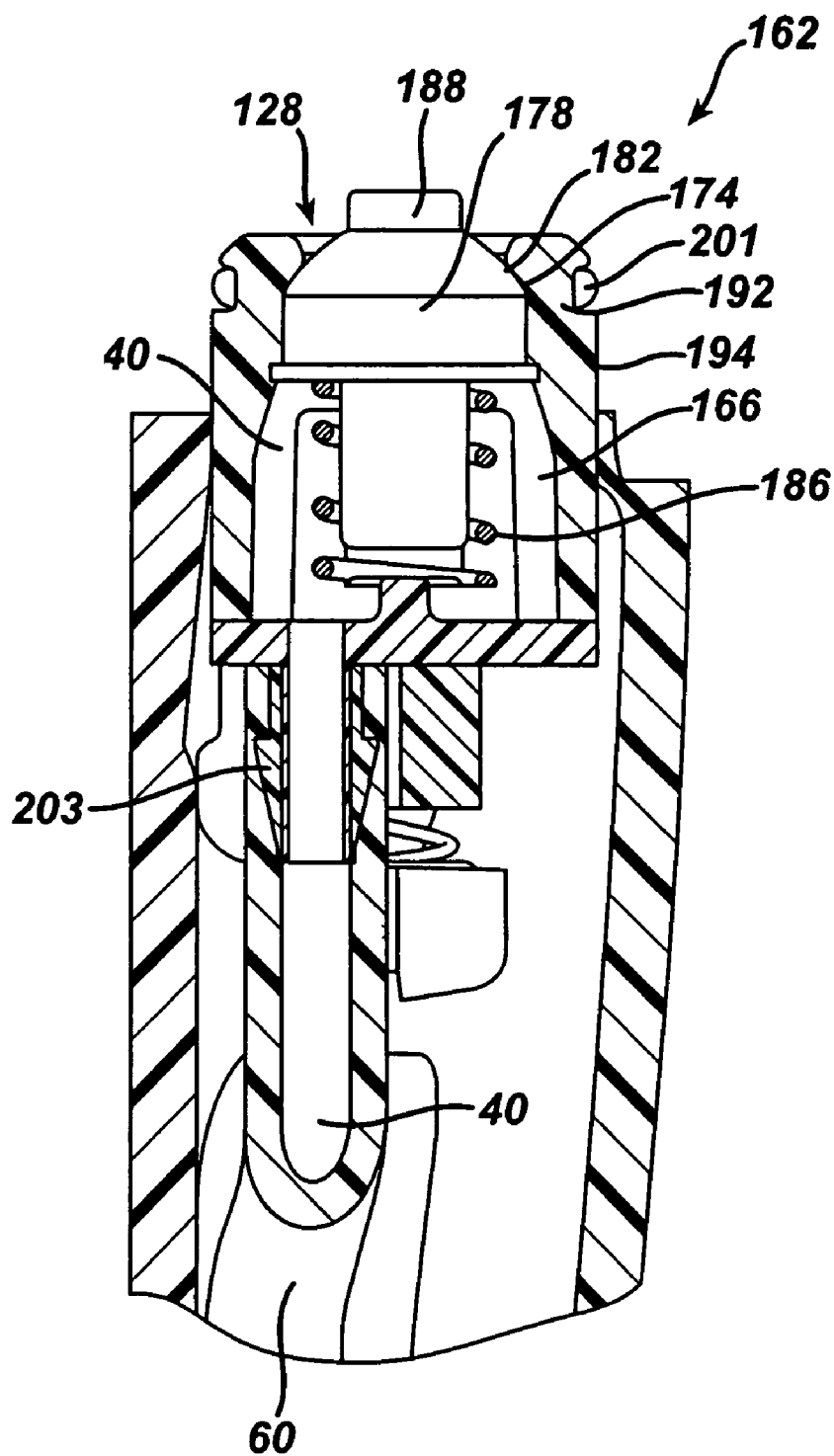
FIGS. 19C and 19D are enlarged detail views of areas C and D, respectively, of FIG. 19B.
Figure 20A:
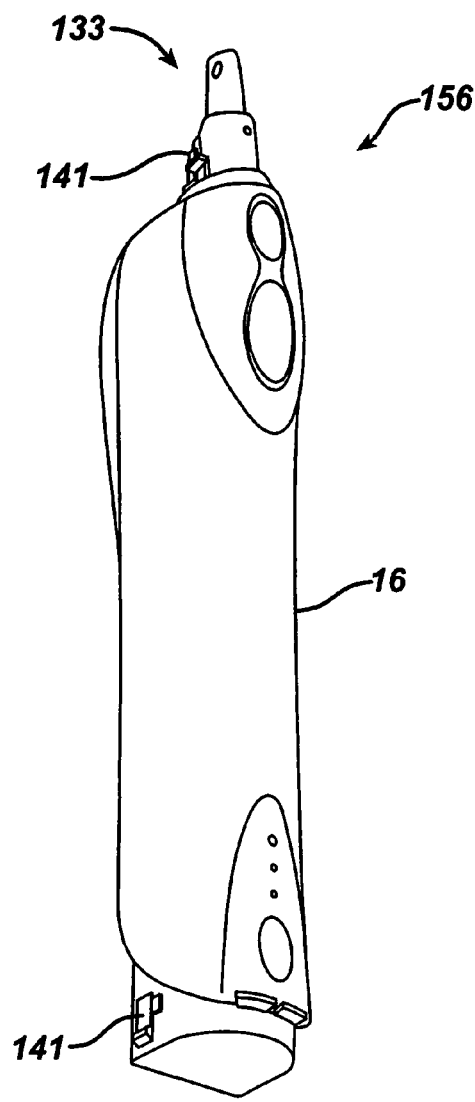
FIGS. 20A and 20C are front and rear perspective views of an embodiment of a separable component forming part of the oral care device of FIG. 2A.
Figure 20B:
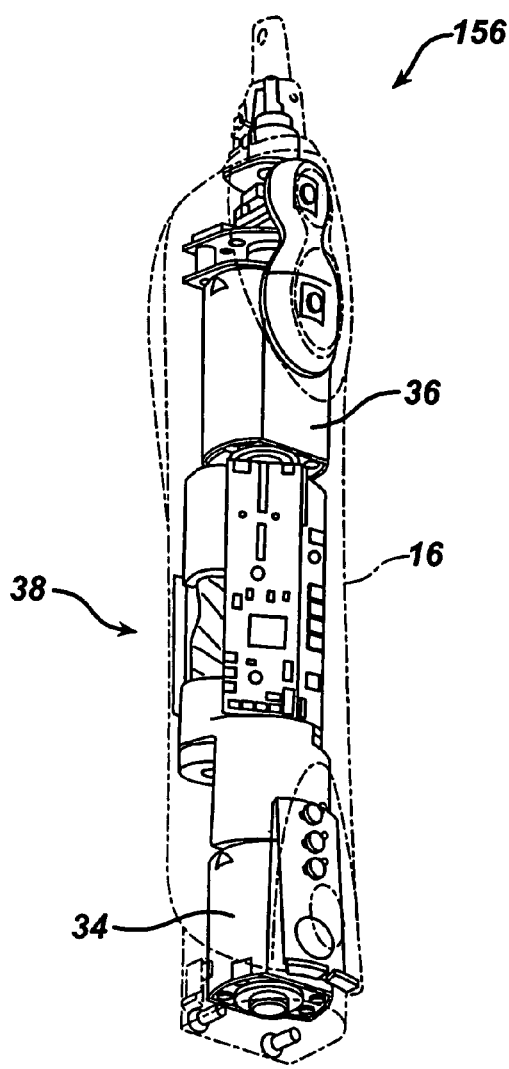
FIGS. 20B and 20D are transparent front and rear views, respectively, of the component of FIG. 20A.

Turning to FIGS. 2A and 2B, oral care device 12 includes a multi-component, separable housing 16 consisting of three interconnected components 152, 154 and 156 (see also for example FIGS. 18A, 19A and 20A). As assembled, the oral care device 12 includes a distal portion 18 at which a head 20 is located and a proximal portion 22 at which a handle 24 is located. Connecting handle 24 and head 20 is neck 26. Head 20 is sized to fit within a user's mouth for brushing, while the handle 24 is graspable by a user and facilitates manipulation of the head 20 during use.

Referring to FIG. 2B, showing a rear view of the oral care device 12, an inlet 28 is positioned near an end surface 30 at the proximal portion 22 of the oral care device. As will be described in greater detail below, the inlet 28 is matable with an outlet 280 (FIG. 23A) located at the docking station 14 for refilling a fluid path within component 154. By positioning the inlet 28 distal of the end surface 30, the inlet is spaced above a seating surface 275 (FIG. 23A) within the receiving portion of the docking station where substances (e.g., dentifrice, water, dust) may accumulate, so that substances will not interfere with mating between the inlet 28 and the outlet 280.

Figure 3A:
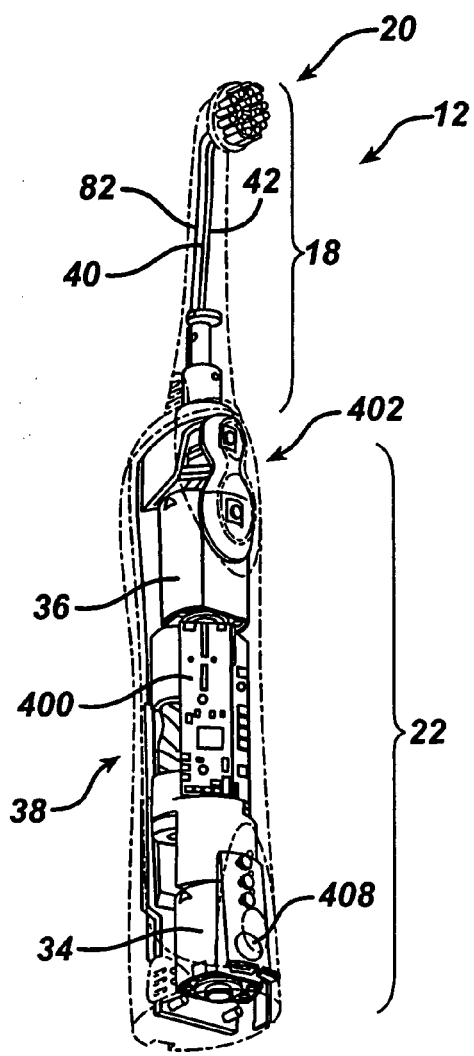
FIG. 3A is a transparent front view of the oral care device of FIG. 2A.
Figure 3B:
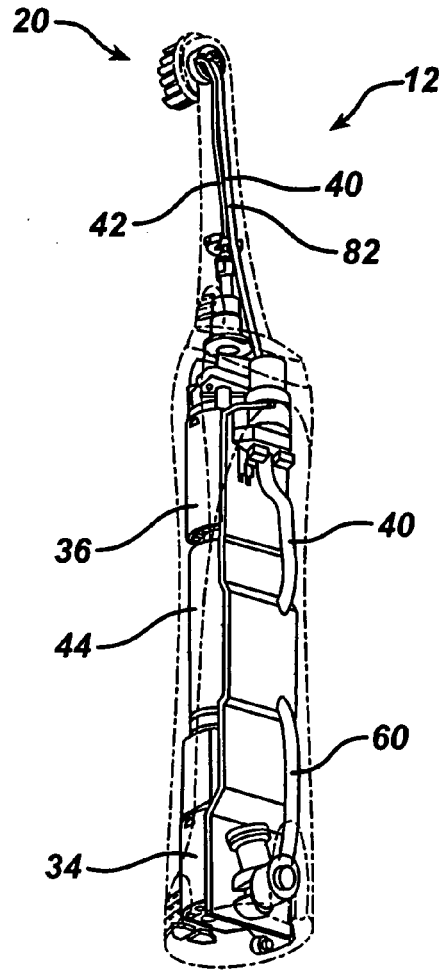
FIG. 3B is a transparent rear view of the oral care device of FIG. 2A.

Referring now to FIGS. 3A and 3B, internal components of the oral care device 12 are shown. Oral care device 12 includes motors 34 and 36. Motor 34 drives a pumping assembly 38, that is used to transfer a fluid along a fluid passageway 40 (see FIG. 3B) toward the distal portion 18 of the oral care device 12. As will be discussed further below, pumping assembly 38 transfers fluid by compressing a portion of tube 60 with a compression element. In some embodiments, motor 34 is reversible and can move fluid in an opposite direction, toward the proximal portion 22 of the oral care device 12. Moving the fluid in the opposite direction may, for example, reduce or, in some cases, even eliminate any leaking of fluid from the head that may occur due to pressure build-up within the passageway. Motor 36 drives a drive shaft 42, which in turn moves (e.g., rotates) the head 20. To supply power to motors 34, 36, a rechargeable battery 44 is electrically coupled to the motors. A suitable rechargeable battery is a Li Ion UR 14500P, available from Sanyo.

Pump Assembly

Figure 4A:
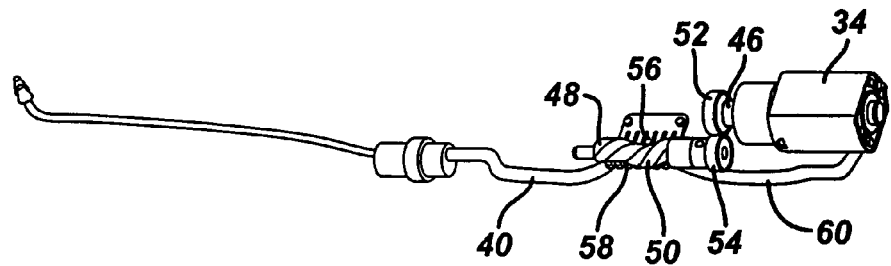
FIG. 4A is a side perspective view of an embodiment of a pump assembly and associated fluid passageway.
Figure 4B:
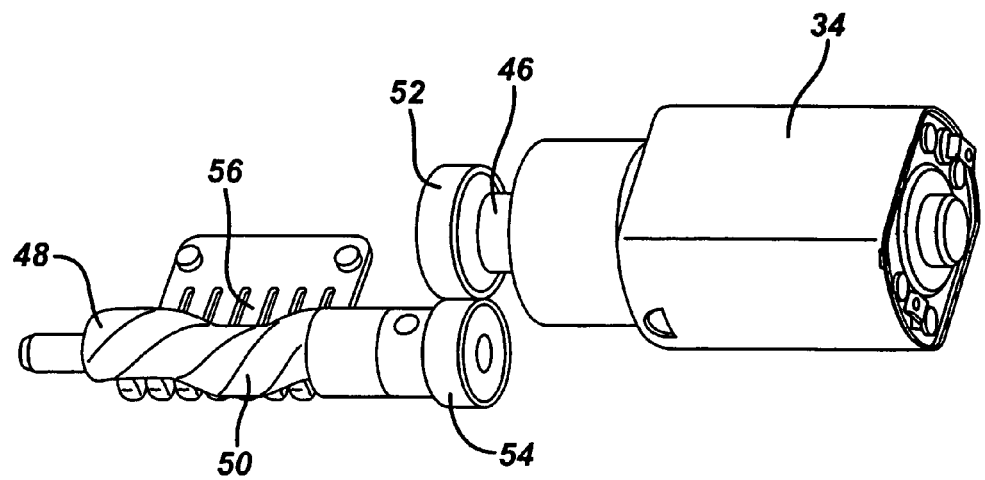
FIG. 4B is a perspective detail view of the pump assembly of FIG. 4A.

As can be seen more clearly in FIGS. 4A and 4B, motor 34 includes a rotatable shaft 46 that is connected to a screw 48 having an advancing, enlarged spiral 50 (FIG. 4B) by a pair of gears 52 and 54. Screw 48 and spiral 50 are shaped to sequentially displace each finger (or compression element) of an array of interconnected fingers 56 as motor 34 rotates the screw. Fingers 56 are secured to an inner wall of the housing 16 (FIG. 2A) forming a series of cantilevered projections that are positioned adjacent tube 60 within a compressible region 58 (FIG. 4A) that, itself, forms a portion of the fluid passageway 40. When the fingers 56 are displaced, they compress the tube 60 within the compressible region 58 progressively along its length in a series of multiple compression events to force fluid along the fluid path (see FIGS. 7A-7E).

Generally, the motor 34 and the gearing (e.g., gears 52 and 54) can be selected as desired. A suitable motor 34 is a FF-130SH, available from Mabuchi. In some embodiments, the gearing is selected to reduce speed by about 23:1.

Figure 5A:
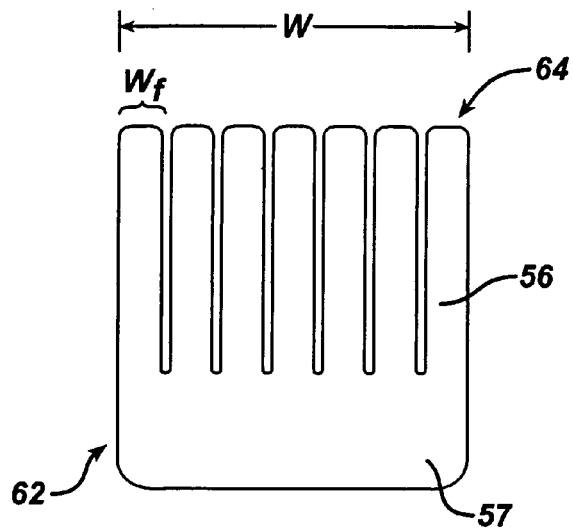
FIGS. 5A and 5B are front and side views, respectively, of an embodiment of an array of compression elements.
Figure 5B:
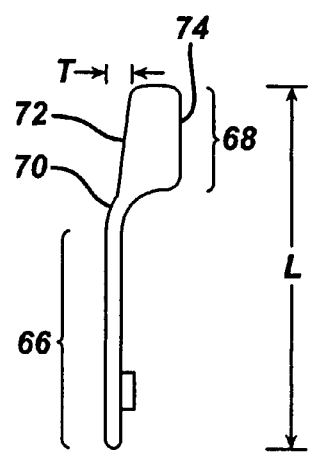

Referring now to FIGS. 5A and 5B, as shown, the array of fingers includes seven interconnected fingers 56 that extend integrally from a common base 57. While seven fingers are depicted, the number of fingers can be selected as desired (e.g., greater than one finger, up to 10, 50, 100 or 200 fingers). Multiple arrays can also be used. The fingers 56 are interconnected at one end 62 and each extends to a free end 64 that can be displaced depending on the angular position of screw 48. While the pump assembly 38 may be used without fingers 56 (e.g., spiral 50 of screw 48 may be used to compress tube 60 within the compressible region 58 directly), by utilizing fingers 56, rolling and sliding wear against the tube 60 within the compressible region 58 can be reduced due to the displacement of the fingers in a direction substantially perpendicular to the long axis of the tube 60. Such a reduction in rolling and sliding wear can reduce potential for rupture of tube 60 that can lead to fluid leakage within the housing 16.

Generally, the sizes and dimensions of each of the fingers can be selected as desired. As shown, each of the fingers 56 is of substantially identical dimensions having a width $W_f$ (e.g., from about 0.05 inch to about 0.2 inch, such as about 0.1 inch) and a length L (e.g., from about 0.4 inch to about 0.6 inch, such as about 0.5 inch) and is shaped to reduce the volume occupied by the fingers within the housing. Referring particularly to FIG. 5B, the fingers 56 extend relatively linearly within regions 66 and 68, with region 68 offset from region 66 a distance T by a bend 70. In operation, surface 72 of fingers 56 can contact an outer surface of the tube 60 and opposite surface 74 can contact screw 48 or vice versa. The offset can ensure that a downward force of the finger is fully applied to the tube 60. In some embodiments, one or more of the fingers may have a differing dimension.

Design of the fingers 56 depends, at least in part, on the screw design and tube 60 design. Each finger 56 is designed to compress a region of the tube 60 that is roughly equal to the width of the respective finger 56. The distance between each finger and the adjacent finger is minimized (e.g., about 0.015 inch) for pumping efficiency.

In general, materials for forming the fingers 56 can be selected as desired. Materials preferable for forming the array of fingers include elastic materials having high resistances to fatigue failure (e.g., due to the repeated displacement of the fingers) and capable of withstanding, at least for a reasonable time (e.g., 180 uses or more), the rolling and sliding contact between the fingers 56 and the spiral 50. A suitable plastic material is DELRIN® plastic. Any suitable method can be employed for forming the fingers, such as molding (e.g., injection molding), casting and machining.

Figure 6A:
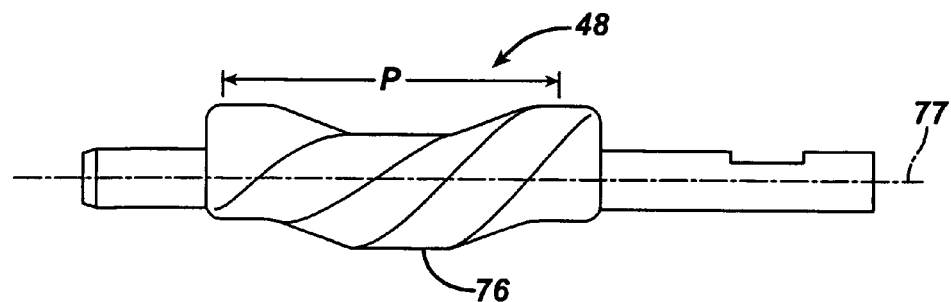
FIGS. 6A and 6B are side and perspective views, respectively, of a screw embodiment.
Figure 6B:
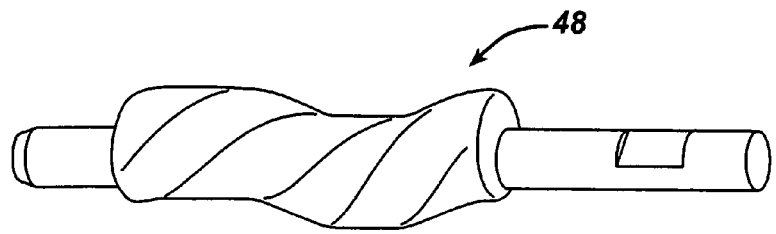

Referring now to FIGS. 6A and 6B, the defining variables of the screw 48 include the pitch of the screw, the dwell time caused by the flat 76 at the top of the pitch. Other variables affecting screw design include the width of the fingers and the number of fingers. The screw pitch P (i.e., the distance center-to-center between flats 76 along a line parallel to shaft axis, at least in some cases, ensures that at least one (preferably more than one) finger compresses the tube at a given moment in time. As shown, P is about 0.8 inch, while the width of each flat is about 0.035 inch.

Generally, the dimensions of the screw 48 can be selected as desired. Preferably, however, the screw 48 design depends, at least in part, on the design of the fingers 56 and the design of the tube 60 within compressible region 58 in order to achieve pumping action to transfer fluid along the passageway 40. As discussed above with regard to the fingers, materials preferable for forming the screw can endure, at least for a reasonable time (e.g., 180 uses, or more), the rolling and sliding contact between the spiral 50 and the fingers 56. A suitable plastic material is DELRIN® plastic. Any suitable method can be used to form the screw 48, such as molding (e.g., injection molding the screw or over-molding plastic onto, for example, a metal shaft) and machining.

Referring to FIGS. 7A-7E, diagrammatic illustrations of portions of a displacement sequence are shown for the pump assembly 38 shown in FIG. 4A and described above. In this displacement sequence, the fingers 56 of the array are sequentially displaced by the enlarged spiral 50 (see FIG. 4B). Prior to compression, within compressible region 58 the tube 60 has a substantially constant inner and outer diameter, and an initial, uncompressed volume $V_0$ for a length L (i.e., the length of the compressible region 58), with L being substantially equal to the width W of the array of fingers (FIG. 5A). When the fingers 56 compress the tube 60, the volume over L decreases to a compressed volume $V_c$. In some embodiments, $V_c$ remains substantially constant during the entire displacement sequence. In certain other embodiments, $V_c$ changes substantially during the displacement sequence. In either case, it is the geometry of the passageway 40 through which fluid flows that is acted on by a series of discrete and progressive compression events to create flow.

Figure 7A:
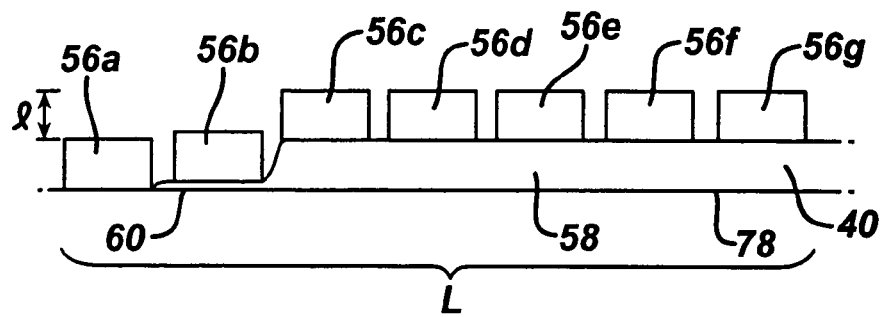
FIGS. 7A-7E illustrate a pumping sequence for the pump assembly and fluid passageway of FIG. 4A.
Figure 7B:
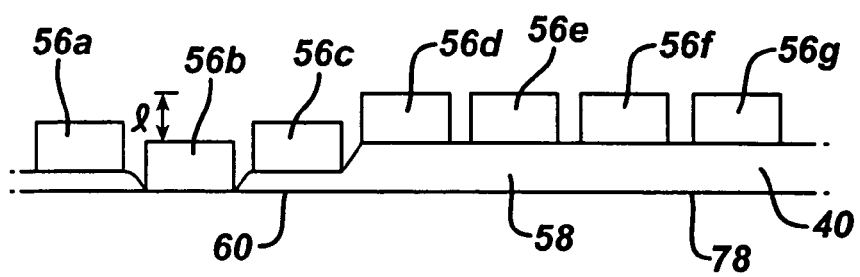
Figure 7C:
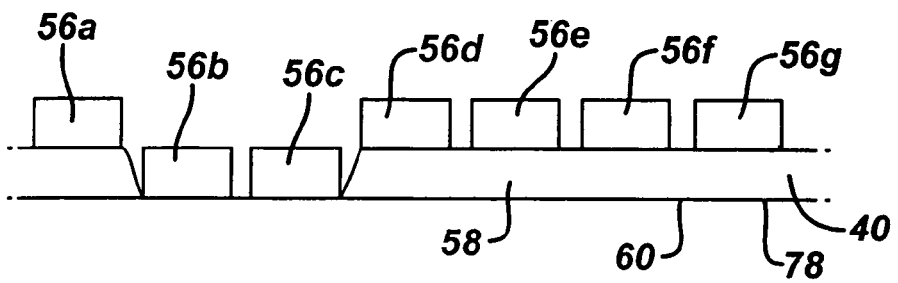
Figure 7D:
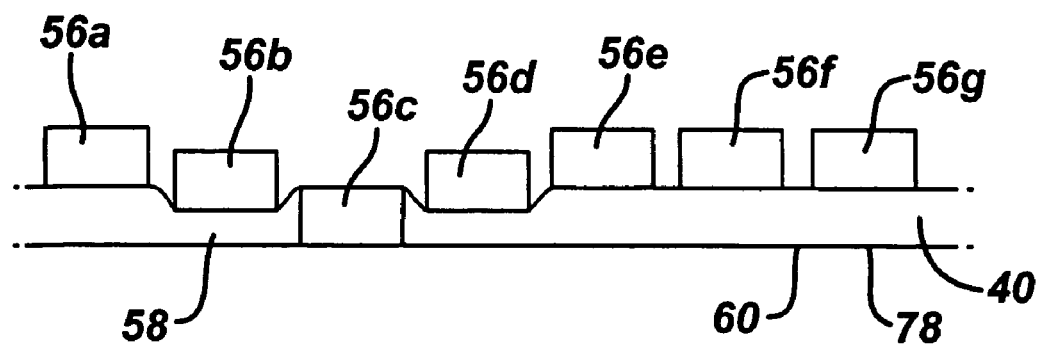
Figure 7E:
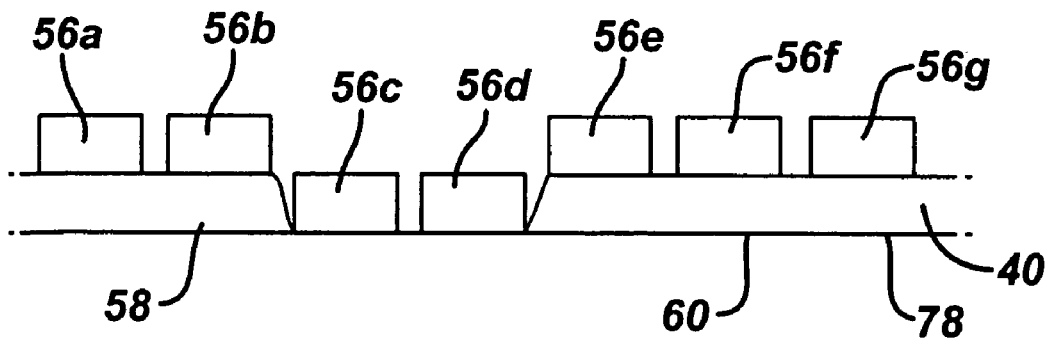

Referring particularly to FIG. 7A, fingers 56*a* and 56*b* are displaced by screw 48 due to the increased diameter of spiral 50 (FIGS. 6A and 6B), which, in turn, compresses (e.g., occludes) a portion of tube 60 within the compressible region 58 between the finger 56 and the wall 78 to positively displace fluid along the passageway 40. While the screw 48 displaces finger 56*a* (eventually a maximum distance l), the screw 48 also displaces finger 56*b*. As the screw 48 turns, referring also to FIG. 5B, finger 56*a* begins a return, drawing fluid into the previously displaced region of the tube 60, while finger 56*b* is displaced the distance l and finger 56*c* begins its displacement. As shown by FIG. 7C, spiral 50 is shaped such that finger 56*b* is displaced the distance l (or the maximum displacement distance) at least from the moment finger 56*a* begins on its return path and at least until finger 56*c* is displaced the distance l. Referring now to FIGS. 7D and 7E, this sequence continues as all seven fingers 56*a*-56*g* are displaced (only the displacement of the first four fingers 56*a*-56*d* is shown, for brevity) and then repeats until the motor 34 stops rotating the screw 48. By displacing more than one finger at all times, the displacement sequence compresses the tube 60 relatively continuously along the length L, with relatively little, if any, backflow. Minimizing backflow generally eliminates the need for a check valve to achieve pumping action. In some embodiments, l is substantially equal to or greater than the inner diameter of the tube 60 in the compressible region 58, however, l can be less than the inner diameter of the tube 60 within the compressible region 58. As shown, the inner diameter of the tube 60 in the compressible region is about 1/16 inch and l is slightly greater than 1/16 inch.

Figure 20C:
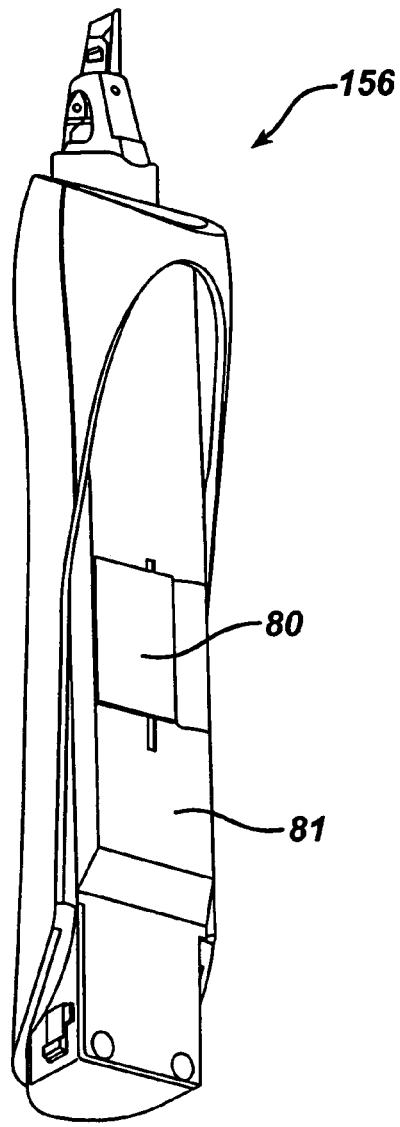
Figure 20D:
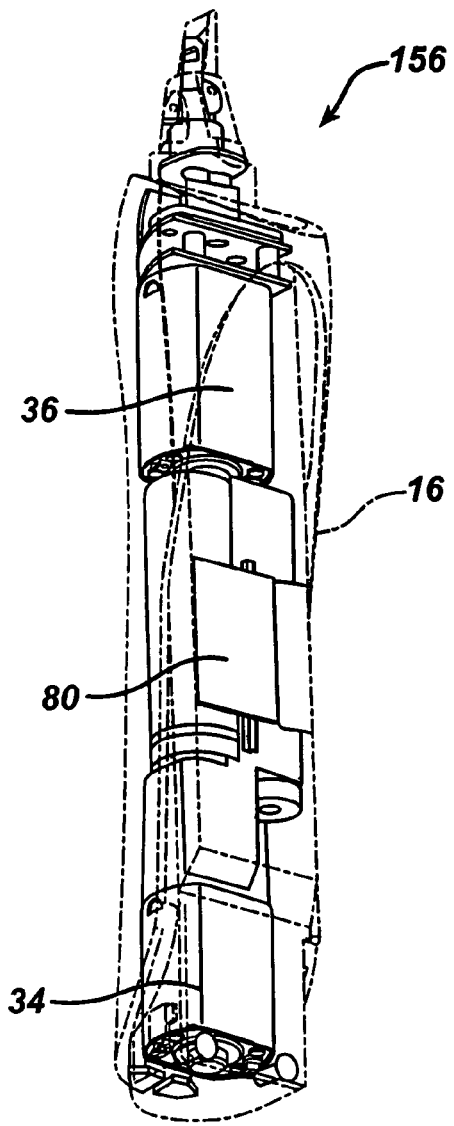

Referring to FIG. 8, flexible membrane 80 may be positioned between the fingers 56 and the tube 60 (see FIGS. 20C and 20D). The membrane 80 is used to seal the internal components positioned within housing component 156 from water, paste or other liquids associated with brushing. The membrane can be, for example, adhered to inner wall 81 of component 156 and/or over molded on the component 156. Referring to FIGS. 9 and 9A as examples, in some embodiments, the membrane 80 includes a compression element 57 or array of compression elements (or multiple arrays of compression elements) that can be used for compressing the tube 60, replacing the fingers 56. Additionally, other compression means are contemplated to compress tube 60 directly (or to displace the compressible elements), such as a spinning bent wire (e.g., a coiled wire or cam/crank shaft wire), solenoids, pneumatic cylinders, a rocking mechanism and/or annular constrictions with ferrofluids.

By utilizing the above-described pump assembly, fluid can be positively displaced without backflow and, as mentioned, without any need for a backflow-preventive device, such as a check valve (although a check valve can be used, if desired). The pump assembly described above is particularly well suited to pump slurries, viscous, shear-sensitive and aggressive fluids. Additionally, the fingers, motor, gears, screw, and other internal components can be isolated from the fluid as the fluid travels along the passageway 40, which, in some cases, can increase the life span of the oral care device 12.

Head Drive Assembly

Referring back to FIG. 3A, motor 36 moves (e.g., translates linearly) pivoting drive shaft 42, which in turn moves (e.g., oscillates rotationally) rotatable head 20. The drive shaft 42 is connected to the rotatable head 20 using an offset design that facilitates placement of a fluid outlet at the head 20 and a tube 82 forming a portion of fluid passageway 40 within the neck 26 of the housing 16. This offset design will be described in further detail below.

Figure 10A:
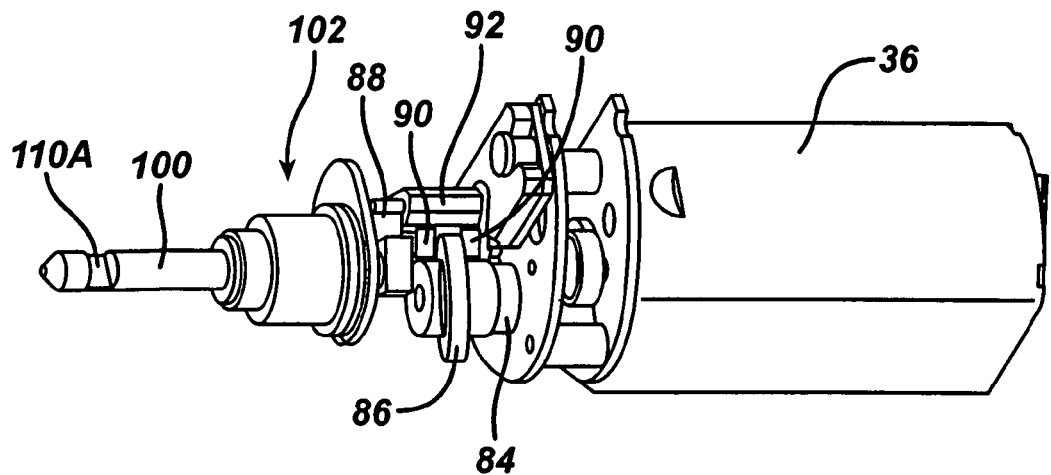
FIG. 10A is a perspective top view detailing an embodiment of a drive assembly.

Movement of the rotatable head 20 is accomplished, in part, by use of a cam and follower system that translates rotational output of the motor 36 into linear motion used to drive the drive shaft 42 backward and forward. Referring particularly to FIG. 10A, a track 86 extends outwardly from a shaft 84 that is connected to the motor 36 by a series of interconnected gears. Follower 88 includes a pair of projections 90 that are designed to ride track 86 as shaft 84 is rotated by motor 36. Track 86 is shaped such that as shaft 84 rotates, the follower 88 oscillates linearly. An alignment component 92 aids in aligning the follower 88 as it oscillates. Although a raised track-follower system is shown, any suitable system can be utilized, such as various other cam systems, including drum cams with followers and grooved tracks with followers. For example, referring to FIG. 10C, an alternative cam design includes a cam 94 having cam geometry on an internal surface 96 of a cup 98. In some cases, the cam follower can run axisymmetric with the motor. Non-cam systems can also be used, such as a belt or chain system. A belt or chain system can replace the drive shaft system shown to drive the head 20 while leaving the axis of the oral care device 12 available to make way for the fluid passageway 40.

Connected to follower 88 is an intermediate drive shaft 100. Intermediate drive shaft 100 is slidably positioned within a guide assembly 102 that is secured directly to the housing 16. Referring to FIG. 10D, the guide assembly 102 includes a gasket 104 (e.g., formed of rubber), a bushing 106 (e.g., a bronze oilite bushing) and a mounting plate 108. The mounting plate 108 is secured to the housing 16 (see FIG. 10B). The guide assembly 102 provides alignment and stabilization for the intermediate shaft 100 as the intermediate shaft 100 moves forward and backward with the follower 88.

Figure 10B:
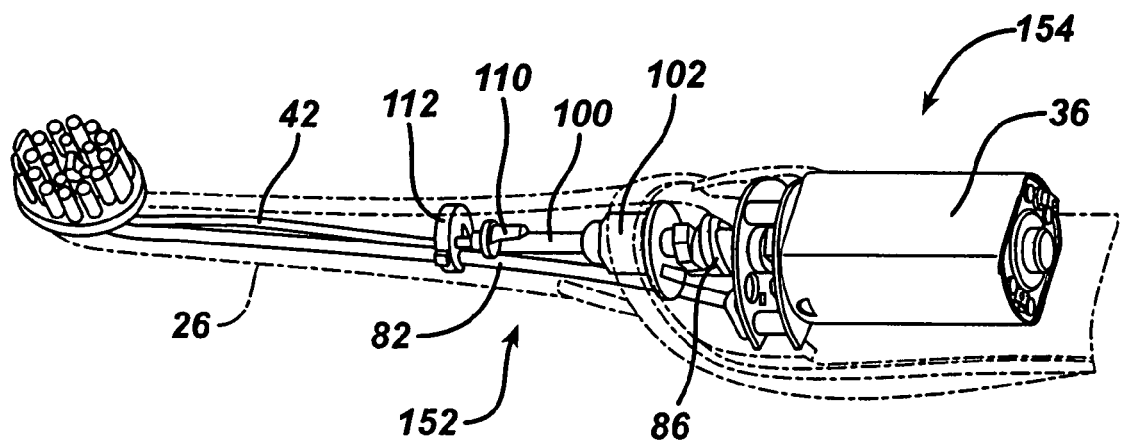
FIG. 10B shows the drive assembly of FIG. 10A positioned within the oral care device.
Figure 10C:
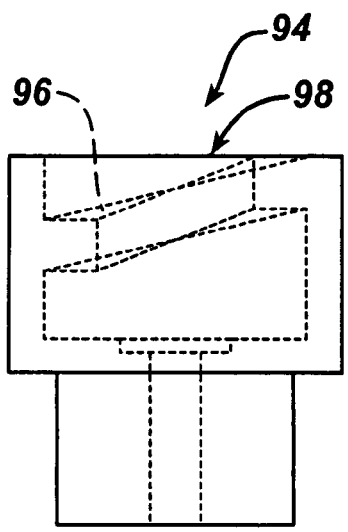
FIG. 10C is a side view of an alternative cam embodiment.
Figure 10D:
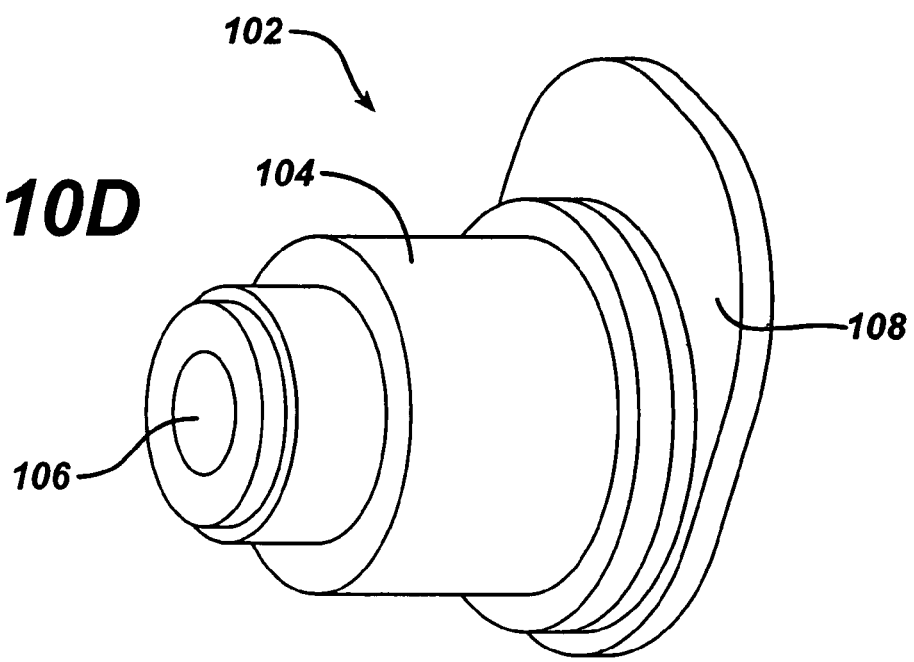
FIG. 10D is a perspective view of a guide assembly.
Figure 11:
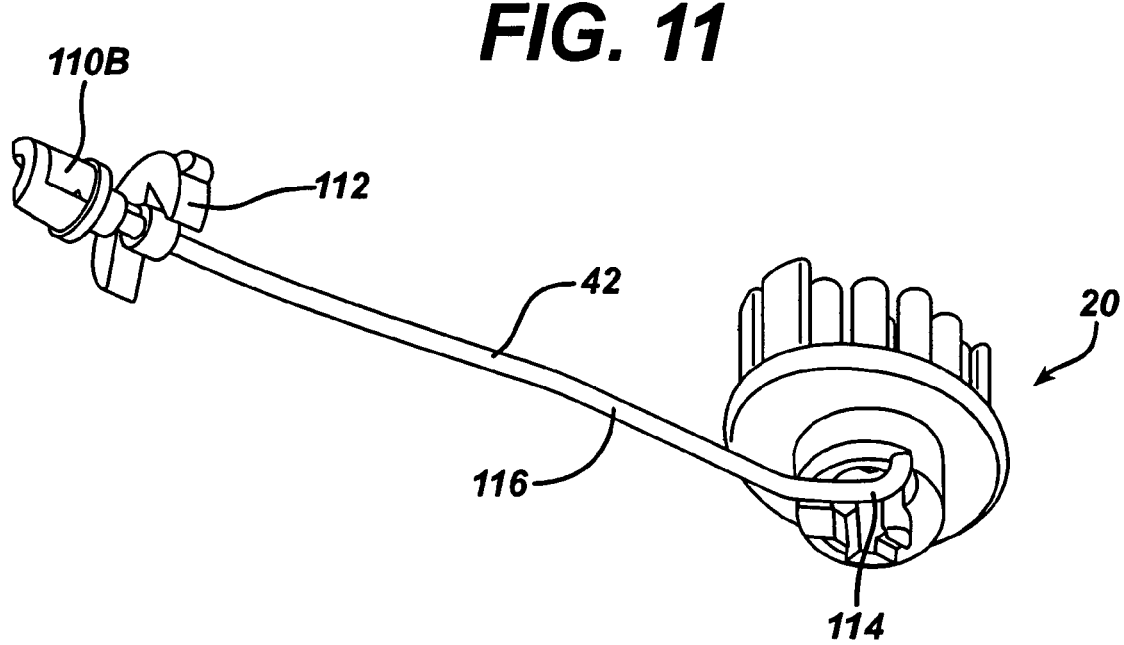
FIG. 11 is a rear perspective view of an embodiment of a drive shaft.

Referring to FIG. 10B, a pivoting drive shaft 42 is coupled to the intermediate drive shaft 100. The drive shafts 100 and 42 are coupled by a pair of interconnecting notches 110A, 110B, which are constructed to engage each other. Notch 110A is positioned at an end of the shaft 42 (FIG. 11) and notch 110B is positioned at the adjacent end of intermediate shaft 100 (FIG. 10A). Drive shaft 42 is slidably positioned within a bracket 112 that is secured within the neck 26 of the housing 16 (shown in phantom) to restrict side-to-side movement of shaft 42 and to maintain the connection between the notches 110. The notches 110 are detachable (e.g., to separate components 152 and 154) by applying a force (e.g., by a consumer) to the bracket 112 in a direction that separates the notches 110. The bracket 112 has sufficient flexibility to allow the notches 110 to detach when pushed on by a consumer to allow the consumer to separate component 154 from components 152 and 156.

As can be seen, the available space within the neck 26 of housing 16 is relatively limited. As a result, the drive shaft 42 is shaped to facilitate placement of both the fluid-carrying tube 82 and the oscillating drive shaft 42 within the neck 26 of the housing 16. Shown more clearly in FIG. 11, the drive shaft 42 includes a number of bends 114, 116 that aid in maintaining the distance between the fluid passageway 40 and the drive shaft 42 so that the tube 82 does not interfere with motion of drive shaft 42. The short bend 114 is connected to rotatable head 20 and is designed to be short enough to be assembled through the neck 26 of housing 16. This can allow the shaft 42 to be assembled through an opening in the bottom of component 152 (see FIG. 10B) and facilitates use of a relatively narrow, unitary housing component 152. The bend 114, however, is long enough to drive the rotatable head 20. By including bends 114, 116, there is a reduced probability that the drive shaft 42 and tube 82 will interfere with each other's operation in use.

Figure 12:
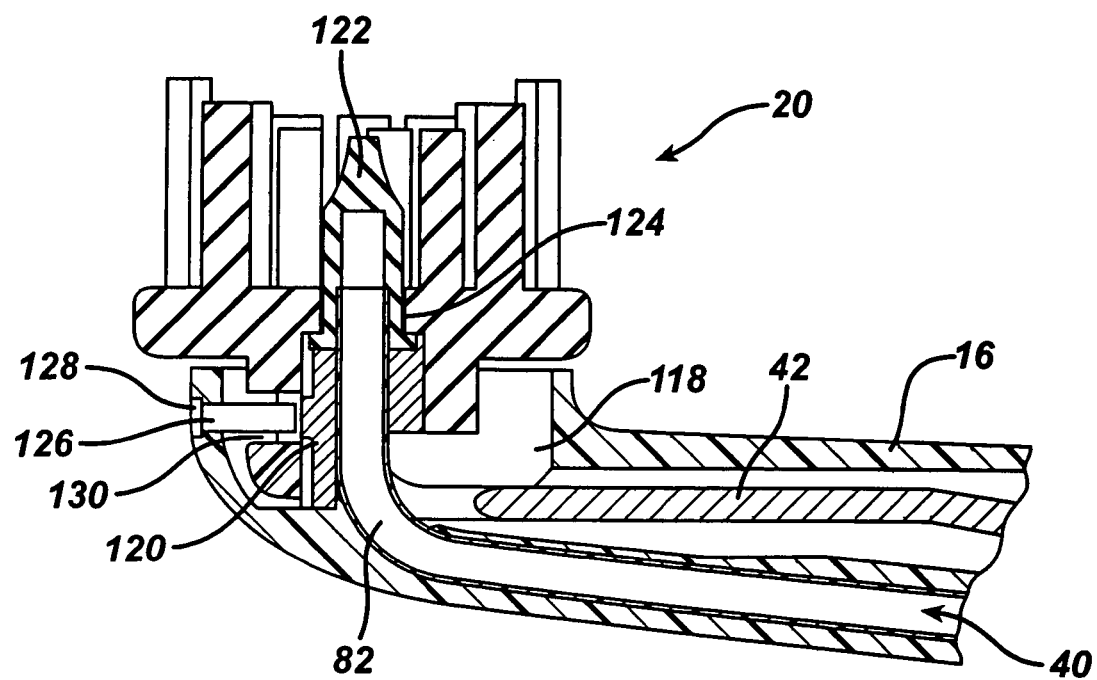
FIG. 12 is a sectional drawing of a head of the oral care device of FIG. 2A.

Referring now to FIG. 12, rotatable head 20 is rotatably connected to housing 16 within a socket 118 formed in housing 16. A non-rotatable fitting (e.g., a bushing) 120 is secured over a distal end of the tube 82 and a valve 122 is fitted over the fitting 120. The valve 122 and fitting 120 extend through an aperture 124 in the rotatable head 20 such that, of the valve 122 and the fitting 120, the non-rotatable fitting 120 receives much of forces from the rotatable head 20 during operation, thus reducing wear and tear on the valve. A pin 126 secures the rotatable head 20 in the housing 16 by passing through a hole 128 in the housing 16 and into a slot 130 formed in the rotatable head 20. This pin 126 and slot 130 connection secures the rotatable head 20 within the housing 16 and allows the rotatable head 20 to rotate.

Figure 13A:
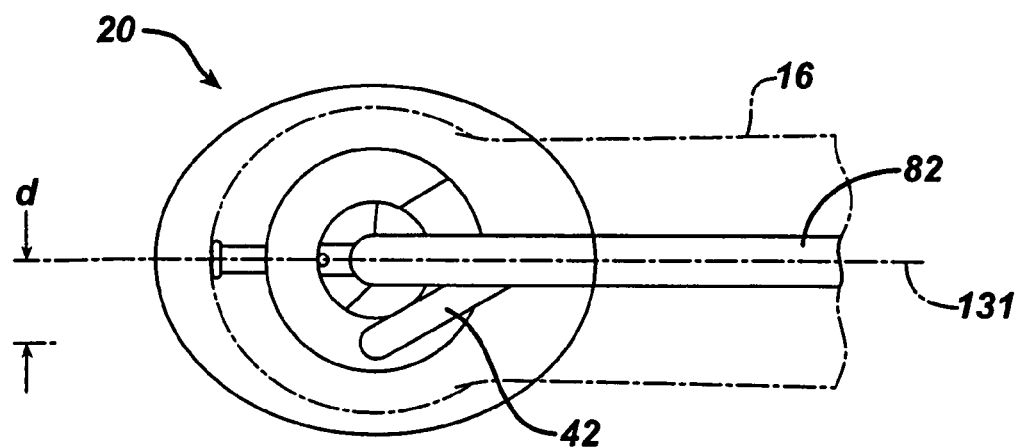
FIGS. 13A and 13B are top and perspective views, respectively, of the drive shaft of FIG. 11 and a fluid passageway connected to the head.
Figure 13B:
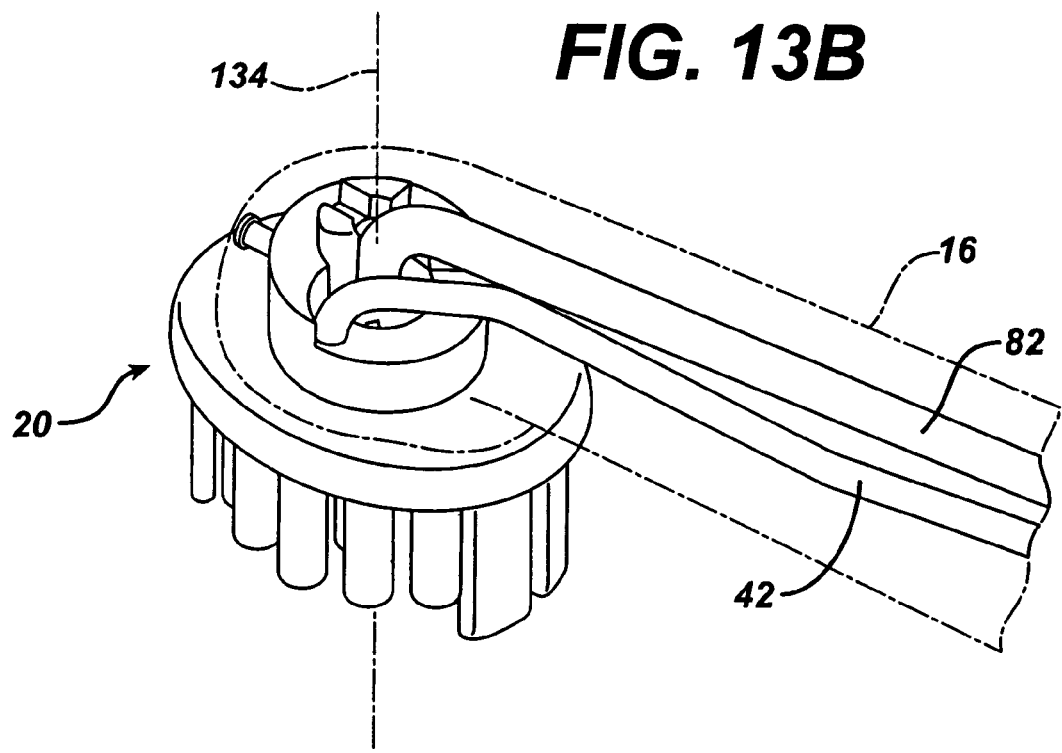

Referring also to FIGS. 13A and 13B, the drive shaft 42 is connected to the rotatable head 20 at a hole (not shown) formed in the rotatable head 20 and positioned offset from a longitudinal axis 131 by a distance d (e.g., greater than zero, such as from about 0.05 to about 0.2 inch, such as about 0.125 inch). The longitudinal axis 131 is perpendicular to an axis of rotation 134 (FIG. 13B) of the head, and distance d is measured perpendicularly from the longitudinal axis 131 to the center of the hole. The shaft 42 is slip fit into the hole to allow oscillation of the rotatable head 20 relative to shaft 42. As drive shaft 42 translates backward and forward, the rotatable head 20 oscillates about axis 134 at a desired frequency (e.g., from about 35 Hz to about 140 Hz, such as from about 50 Hz to about 80 Hz.).

Figure 14:
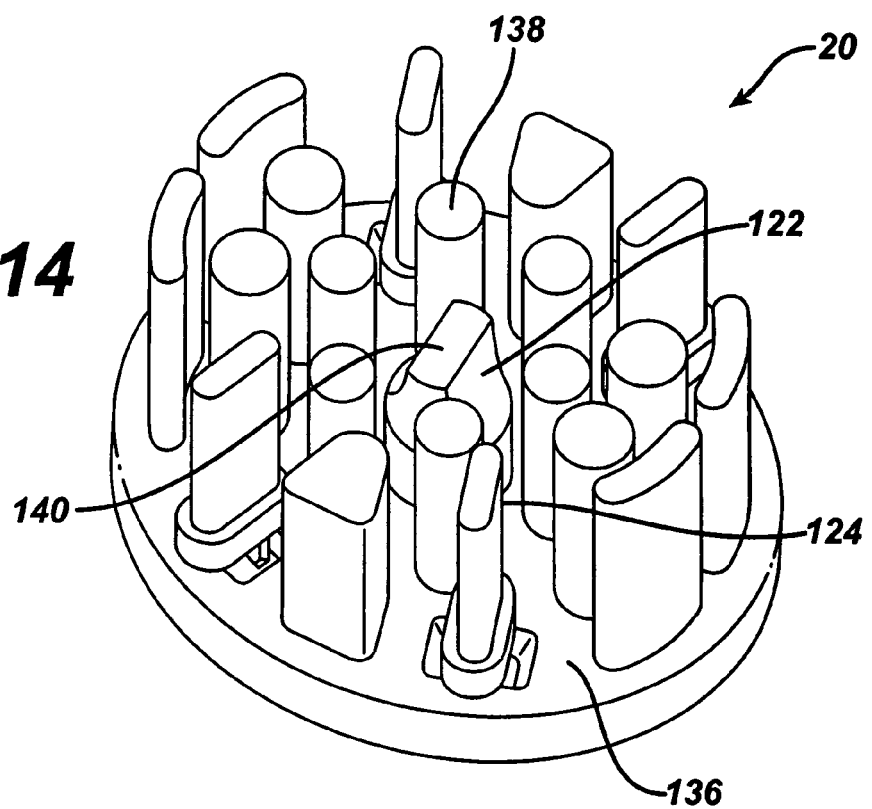
FIGS. 14 and 15 are front perspective views of two brush embodiments.
Figure 15:
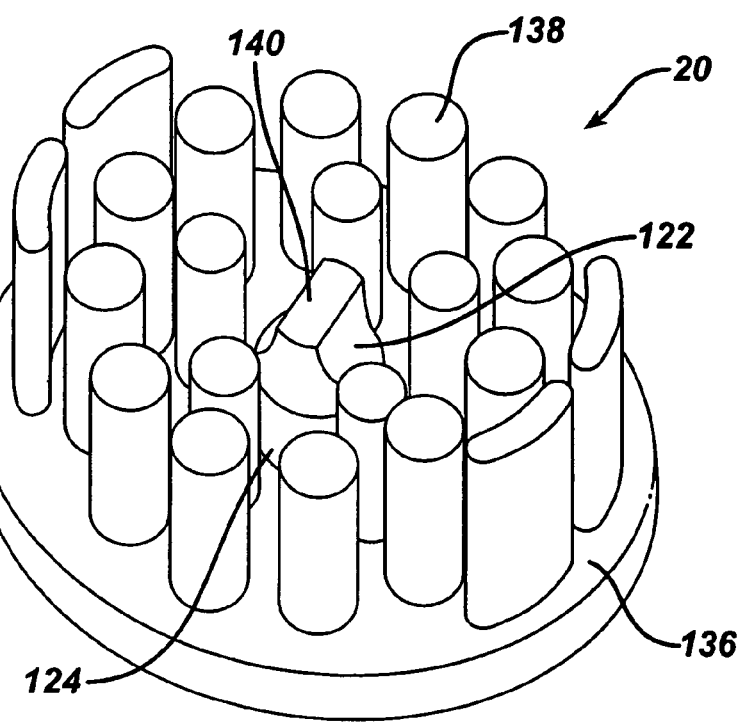

Referring to FIGS. 14 and 15, head 20 includes a base 136 that includes the opening 124 (see FIG. 12) through which the valve 122 extends outwardly beyond the base. Although any suitable valve can be employed, such as a duckbill valve or other types of check valves, the duckbill valve is preferred for ease of use and for reducing the introduction of outside fluids and particles into the fluid passageway (e.g., during use and storage). In some embodiments, the distal end of the tube 82 forms the fluid outlet without use of a valve attached thereto. In some embodiments, opening 124 forms a portion of the fluid passageway.

Extending from the base 136 is a plurality of bristle tufts 138. Although each tuft 138 is shown as a solid mass in the drawings, the tufts are actually each made up of a great mass of individual plastic bristles. The bristles may be made of any desired polymer, e.g., nylon 6.12 or 6.10, and may have any desired diameter, e.g., 4-8 mil. The tufts 138 are supported by the base 136, and may be held in place by any desired tufting technique as is well known in the art, e.g., hot tufting or a stapling process. The tufts 138 may also be mounted to move on the base 136, as is well known in the toothbrush art. For a more detailed discussion of brush heads, Applicants refer to pending U.S. application Ser. No. 10/666,497, filed Sep. 9, 2003, the disclosure of which is hereby incorporated by reference in its entirety.

Generally, tufts 138 and fluid outlet 140 (along with opening 124) may be positioned where desired. Referring to FIG. 14 and FIG. 15, tufts 138 are positioned about centrally located valve 122. Referring particularly to FIG. 14, a contoured ellipse head design is illustrated where base 136 is in the form of an ellipse. The valve 122 is shown positioned at about the center of the elliptical base 136 (i.e., at the intersection of the major and minor axes of the ellipse) with the tufts 138 arranged about the fluid outlet 140 in an elliptical arrangement. FIG. 15 shows a more circular head design with valve 122 positioned at the center of the base 136 and the tufts 138 positioned about the fluid outlet 140 in a circular arrangement.

Figure 16A:
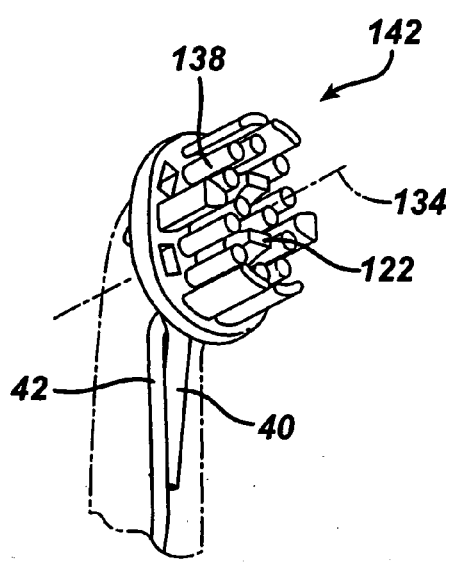
FIGS. 16A and 16B are front and rear perspective views of the head and neck of another oral care device embodiment.
Figure 16B:
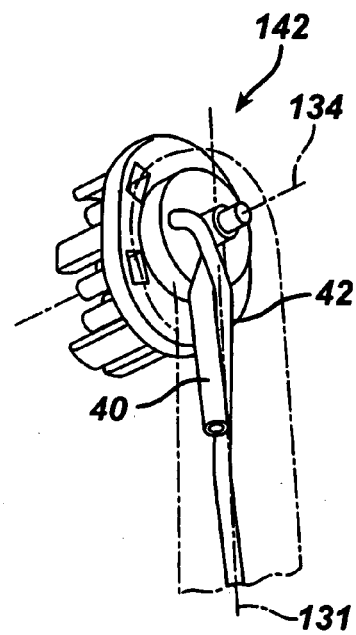
Figure 17A:
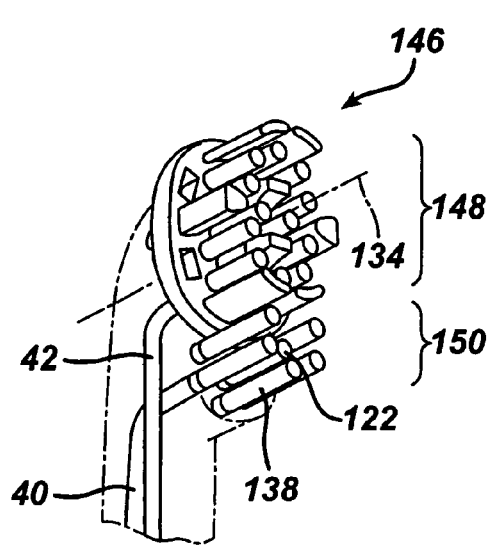
FIGS. 17A and 17B are front and rear perspective views of the head and neck of another oral care device embodiment.
Figure 17B:
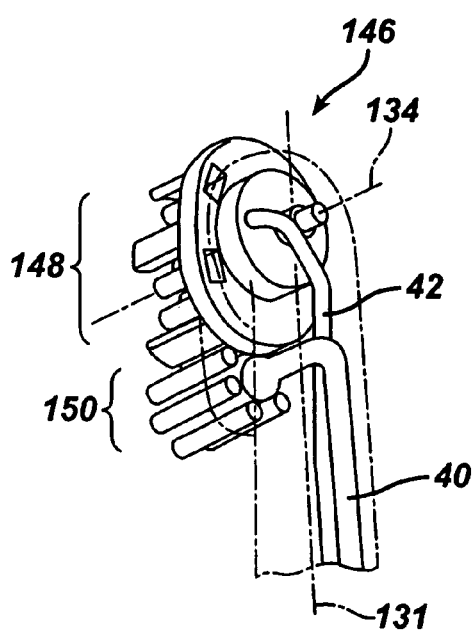

It is not required, however, that the valve 122 and associated fluid outlet 140 be positioned centrally within the rotatable head 20 or that the fluid outlet be aligned with the axis of rotation 134 of the rotatable head 20. For example, referring to FIGS. 16A and 16B, a movable head 142 includes an offset valve design. In this embodiment, a valve 122 and associated fluid passageway 40 extends through a rotatable head 142 spaced from an axis of rotation 134. As above, a drive shaft 42 is connected to the rotatable head 142 offset from a longitudinal axis 131. As another example, referring to FIGS. 17A and 17B, a head 146 includes a movable portion 148 and a stationary portion 150 with a valve 122 and associated fluid passageway 40 positioned in the stationary portion 150. As an alternative, the valve 122 can be positioned within the movable portion 148, as described above, rather than in the stationary portion 150. The movable portion 148 can be formed by a rotatable head that is connected to a drive shaft, as described above. In some embodiments, the drive shaft 42 includes a fluid path that forms a portion of fluid passageway 40 by fluidly connecting the drive shaft 42 to tube 60. An end (not shown) of the drive shaft 42 that is connected to the head can provide a fluid outlet, or a valve or other structure can be attached to the end of the drive shaft.

Valves and Seals

Referring now to FIGS. 18A-19B and 20A-20D, as noted above, housing 16 is separable into three components 152, 154 and 156. Component 152 (i.e. a removable head assembly; FIGS. 18A and 18B) includes movable head 20 and neck 26 along with drive shaft 42 and tube 82. Component 154 (i.e. a removable, refillable cartridge assembly; FIGS. 19A and 19B) includes tube 60, compressible region 58 (FIG. 19B) and inlet 28. Motors 34 and 36 are housed by component 156, along with pumping assembly 38 and rechargeable battery 44 (see FIG. 3B).

Because each of components 152 and 154 contain a portion of fluid passageway 40, in order to reduce or, in some cases, to prevent fluid leakage when components 152 and 154 are separated, each of the components 152 and 154 includes a valve 160 and 162, respectively, having a "normally closed" construction. The valves are disposed at an end of the associated conduit, e.g., to close substantially the entire fluid passageway associated with each component when the components are disengaged.

Figure 18C:
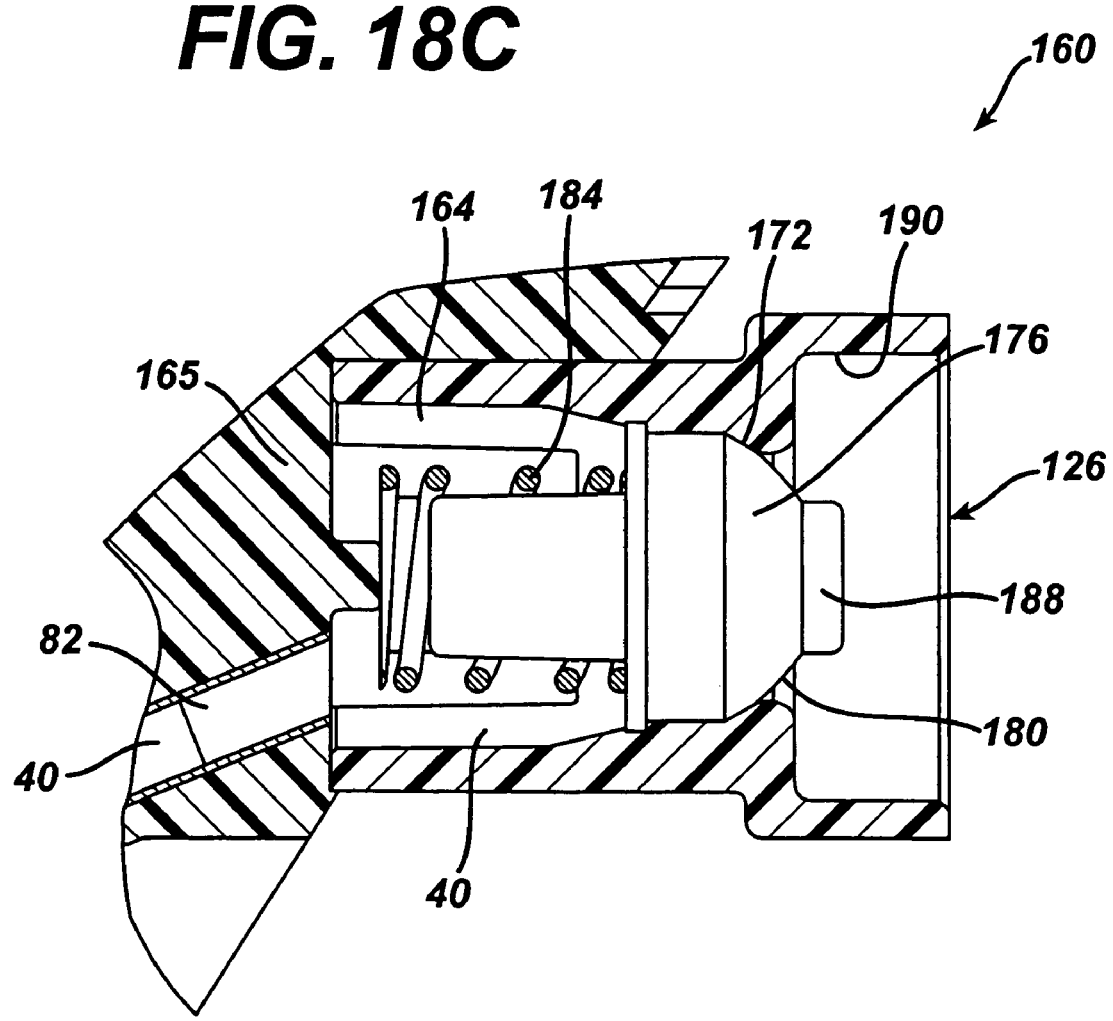
FIG. 18C is a sectional detail view of area C of FIG. 18A showing a valve.

Referring to FIGS. 18A and 18C, the neck valve 160 is capable of mating with the cartridge valve 162 (see FIGS. 19A and 19C). Referring to both FIGS. 18C and 19C, neck valve 160 and cartridge valve 162 include inner surfaces 164 and 166, respectively, that each form a portion of fluid passageway 40. Near openings 126 and 128, inner surfaces 164 and 166 neck-down, reducing the inner diameter of the fluid passageway, to form seating surfaces 172 and 174. Biased against seating surfaces 172 and 174 are poppets 176 and 178. Poppets 176, 178 have outer surfaces 180, 182 that are contoured to complement the contour of the respective seating surfaces 172 and 174. The poppets are biased against the seating surfaces 172, 174 by helical springs 184, 186 (e.g., between about 0.250 and 0.375 inch long with an overall outer diameter of between about 0.120 and 0.240 inch; formed from, e.g., stainless steel wire between about 0.014 and 0.018 inch in diameter) to close the fluid passageway 40 when components 152 and 154 are separated (e.g., forming a fluid-tight and/or air-tight seal). The valves can be constructed to remain closed and seal the passageway even if an amount of positive pressure is applied within the passageway (e.g., the pumping mechanism is activated). As positive pressure is applied to the respective poppet from within the passageway, an increased amount of biasing force is transmitted and the poppet applies more force against the seating surface maintaining the seal.

Figure 19D:
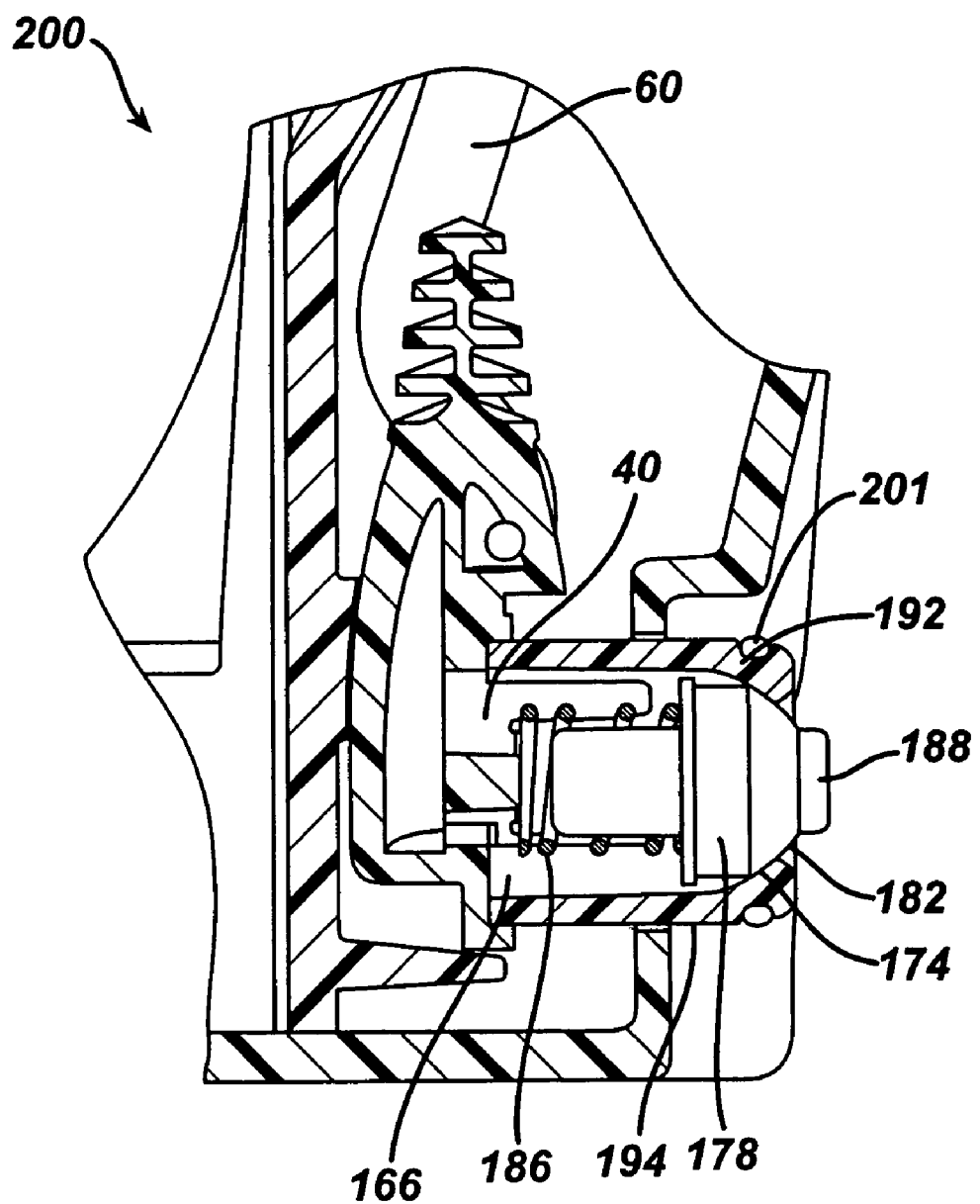
Figure 21:
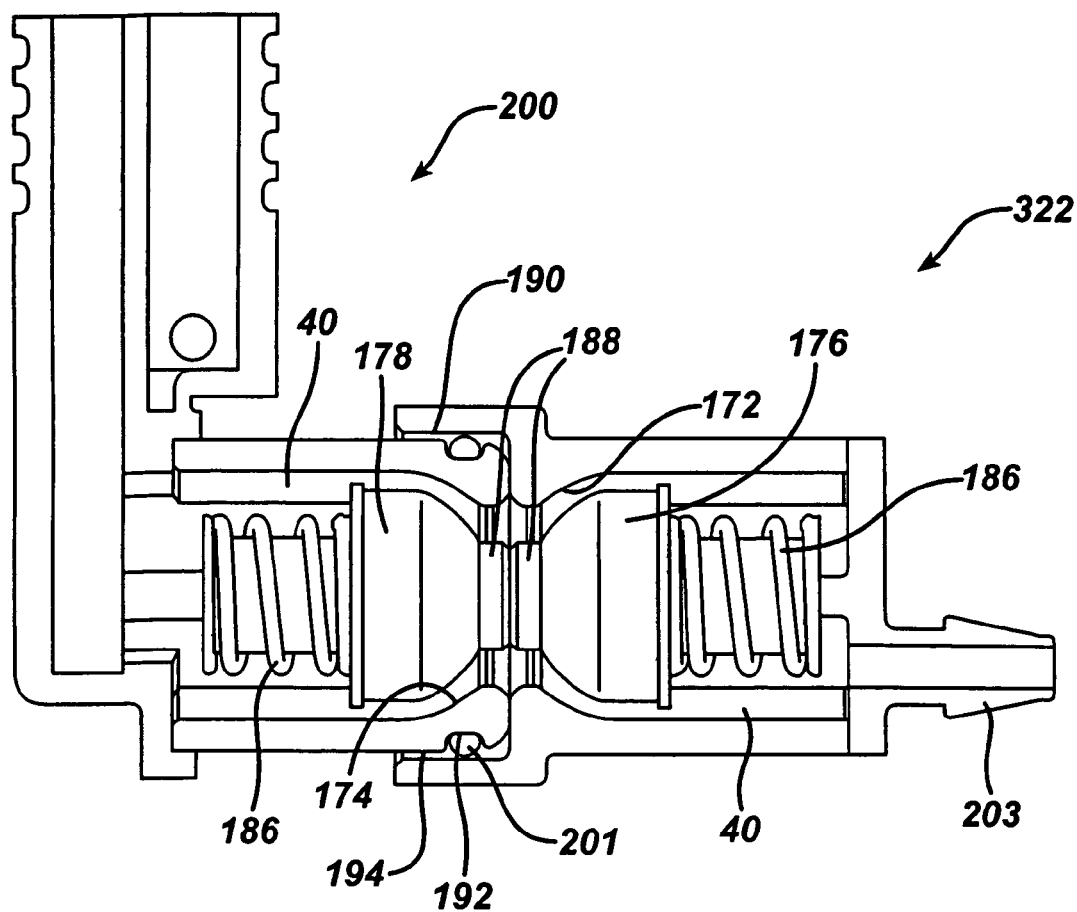
FIG. 21 is a side section view of the valve of FIG. 19D mated with a docking station valve.
Figure 23A:
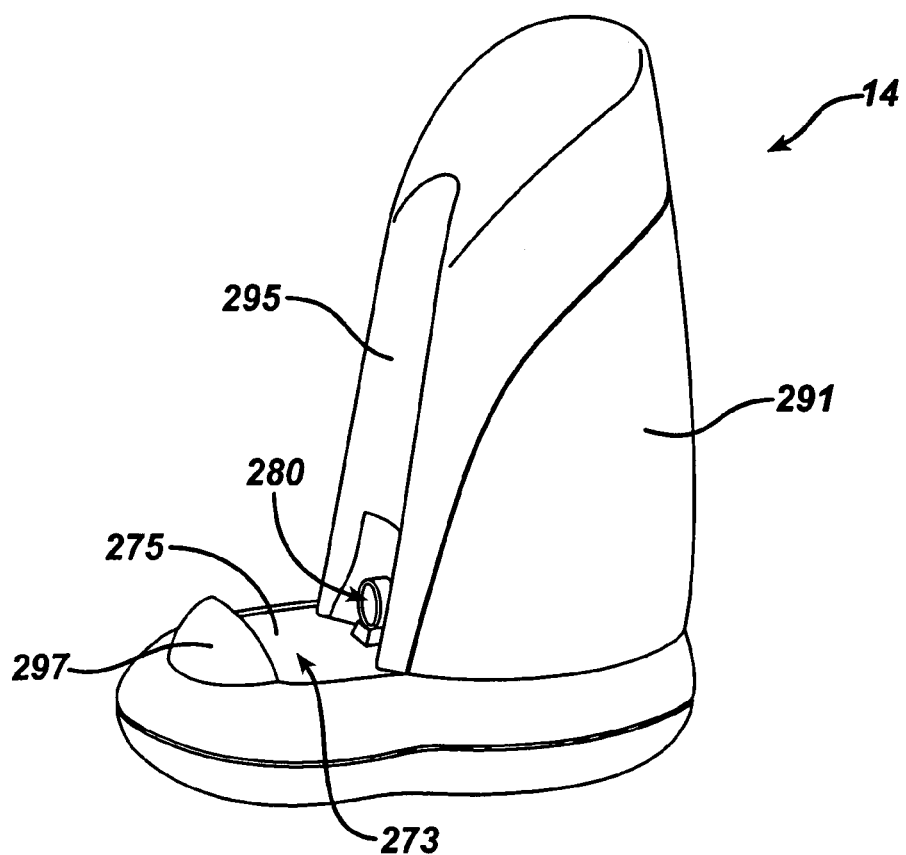
FIG. 23A is a side perspective view of an embodiment of a docking station.

Referring to FIGS. 19B and 19D, the cartridge component 154 includes a second valve 200 that is capable of mating with docking station valve 322 at outlet 280 (FIGS. 21 and 23A). Valve 200 includes the features described above with regard to valve 162, and valve 322 includes the features described above with regard to valve 160. Valve 200 controls fluid flow through the inlet 28 positioned near the base surface 30 (see FIG. 2B), while valve 322 controls fluid flow through the docking station outlet 280. To illustrate operation of the valves, referring to FIG. 21, each of the poppets 176 and 178 include an extended portion 188. The extended portions 188 project beyond the seating surfaces 172, 174 when the valves are separated. When the valves 200 and 322 are mated, the extended portions 188 of the poppets 176, 178 contact each other. In some embodiments, only one or neither of poppets 176, 178 has an extended portion 188 that extends beyond the respective seating surface. As the valves 200 and 322 approach one another, the poppets 176, 178 deflect away from the seating surfaces, thus opening the fluid passageway 40 and allowing the flow of fluid therethrough. When mated, the valves are also constructed to remain open during use as pressure is applied to the poppets, e.g., by fluid flowing within the passageway. This can be accomplished by restricting motion of the respective poppets when the valves are open.

To seal the fluid passageway 40 from the surroundings when the valves are mated, cartridge valves 162 and/or 200 can include a sealing ring 201 (e.g., an O-ring) positioned within a recess 192 extending inwardly from an outer surface 194 of the cartridge valve. In some embodiments, the sealing ring provides a fluid-tight seal, but not an airtight seal. In some cases, the sealing ring provides both a fluid-tight and an airtight seal. The sealing ring can be sized to contact an inner surface 190 of the valves 160 and/or 322.

Referring to FIG. 18C, the neck valve 160 incorporates a portion 165 of the neck 26 as part of the valve assembly. The neck valve assembly 160 is directly connected to the proximal open end of tube 82, allowing fluid passage directly from the valve into tube 82. Referring to FIG. 19C, the cartridge valve 162 is connected to tube 60 by means of a barbed fitting 203 at the rear of the assembly. Other methods of attachment, such as clamps, wire or plastic tie wraps and/or adhesives are also possible.

Figure 22A:
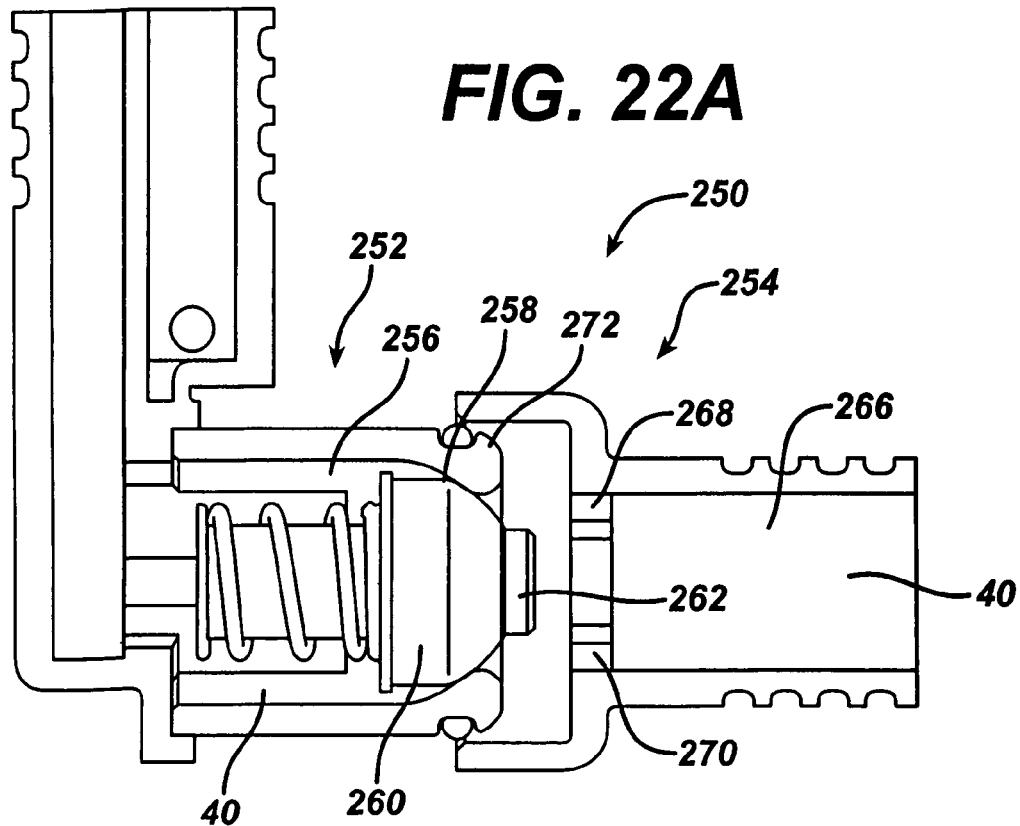
FIGS. 22A and 22B are side section views of another valve assembly embodiment.
Figure 22B:
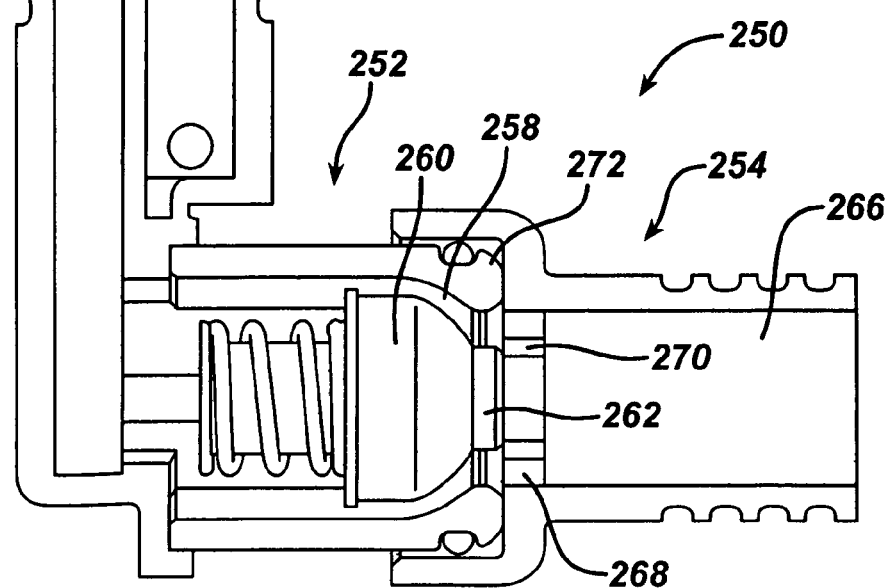
Figure 22C:
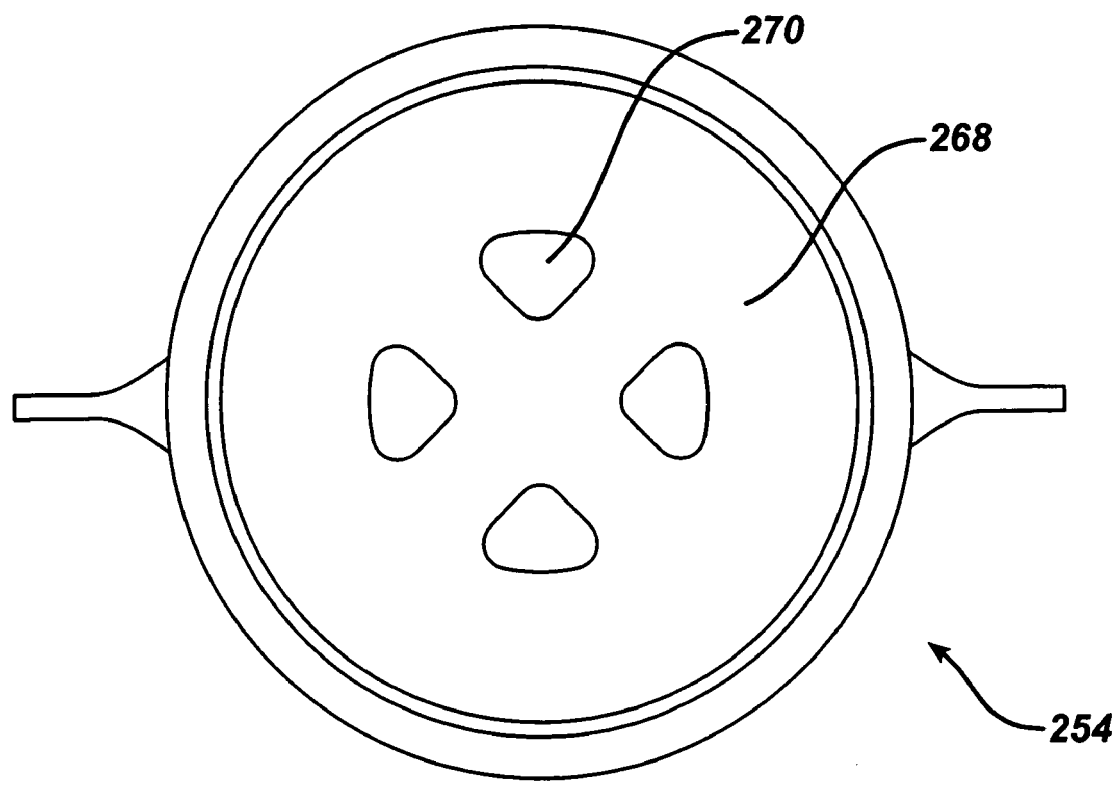
FIG. 22C is a front view of a valve fitment of FIGS. 22A and 22B.

In some embodiments, an alternative valve assembly is used that closes the fluid passageway 40 in only one component, when the components are separated. Referring to FIGS. 22A-22C, a one-sided valve assembly 250 includes a valve 252 and an open fitment 254 (see FIG. 22C). The valve 252 includes an inner surface 256 that is necked-down to form a seating surface 258 and a poppet 260 with an extended portion 262 that is biased toward the seating surface 258. The fitment 254 includes an inner surface 266 forming a passageway for fluid flow and a wall 268 that spans the passageway of the fitment. The wall 268 includes four channels 270 that are in fluid communication with the passageway. The channels 270 provide a conduit through which fluid can flow from the fitment 254 to the valve 252 (or vice versa) when the valve 252 is mated with the fitment 254.

As valve 252 is mated with fitment 254, turning to FIG. 22B, the extended portion 262 is brought into contact with wall 268. As a surface 272 of the valve 252 approaches wall 268, poppet 260 is deflected away from seating surface 258, opening the valve 252. The channels 270 are positioned such that poppet 260 does not block the channels 270 so that fluid can pass therethrough. In some embodiments, the fitment 254 replaces the neck valve 160 (e.g., to allow for rinsing of the passageway 40 within neck component 152).

Generally, the materials for forming the fitment and valves, including the poppets and springs, can be selected as desired. Suitable materials for forming the valves include polyethylene (e.g., HDPE), polypropylene, acrylonitrile-based co-polymer (e.g., BAREX® available from BP p.l.c), acetal (POM), or corrosion resistant metals, such as stainless steel. Suitable materials for forming the poppets include elastomers such as ethylene propylene diene monomer (EPDM), nitrile rubber (NBR), fluorocarbons (e.g., VITON® fluorocarbons, available from DuPont Dow Elastomers L.L.C.), combinations of these materials and any of these materials used in combination with a harder material such as stainless steel. The valves can be formed by any suitable method including molding (e.g., injection molding) and/or machining, with common joining processes such as ultrasonic or laser welding, adhesives and the like.

Components 152 and 154 are designed to be replaceable. By "replaceable", we mean that components 152 and 154 are interchangeable by the consumer with other like components to form an assembled oral care device, and that replacement can normally be effected by the consumer without damage to the oral care device. As can be appreciated from the above description, because the entirety of fluid passageway 40 is carried by components 152 and 154, the entirety of fluid passageway 40 is also replaceable. In other words, any part of oral care device 12 that touches fluid is replaceable. This facilitates use of different types of fluids with the oral care device without undesired mixing of the fluids and repair of the oral care device (e.g., due to fluid passageway rupture, valve malfunction, and the like). This also helps to maintain the oral care device in a sanitary condition during extended use.

To assemble the oral care device 12, components 152 (head assembly) and 154 (cartridge) both attach to component 156 by independent mechanical snap latching mechanisms 137 (FIGS. 2A and 2B). Referring to FIGS. 18A and 20A, component 152 is attached to component 156 by inserting a top end 133 of the component 156 into a receiving end 135 of component 156. In doing so, a mechanical connection is formed by snap latch members 139 (FIG. 18B) and 141 (FIG. 20A), the drive shafts 42 and 100 are connected and, if component 154 is connected to component 156, a fluid connection is made through the valves 160 and 162. Component 154 is attached to component 156 by a similar snap latch connection (see also FIG. 19A). To detach components 152 and 154 from component 156, a user can squeeze the snap latches 137 toward each other to disengage the mechanical connection. This is accomplished by pinching buttons 143 located at the handle 24 to detach component 154 from component 156 and by pinching buttons 143 located at the neck 26 to detach components 152 and 156. Other connections are contemplated, such as an independent screw or bayonet-style collar that can move independently of the orientation of the components being attached. Because both a drive shaft and fluid line connection must be made, a linear connection (e.g., as opposed to a rotational) is preferred to align the two connections. Other general attachment arrangements can be made, such as attaching component 152 to component 154, and subsequently, attaching component 154 to component 156.

Oral Care Device Controls

Referring back to FIG. 3A, the oral care device 12 includes a control circuit or controller 400 that is electrically connected to the motors 34, 36 and that generally governs operation of the motors. A user interface 402 provides external interaction with controller 400. The user interface 402 includes on and off buttons 404 and 406 and a fluid level switch 408, all of which are accessible from exterior of the housing 16 (see FIG. 2A).

While the controller can be programmed as desired, as one example, the controller is designed such that depressing button 404 initiates both motors 34 and 36 and depressing button 406 initiates only one of the motors 34, 36, such as motor 36. By depressing button 404 both head movement and fluid flow can be initiated. By depressing button 406, only one of fluid flow and head movement can be initiated. Depressing button 404 or 406 can also halt the associated motor(s) subsequent to initiation. In cases where button 406 initiates and halts only motor 36, a user can, for example, brush without additional fluid delivery and can rinse the oral care device 12 while the head rotates. The fluid level switch 408 allows a user to choose between preselected rates of fluid delivery, such as high (e.g., about 1.1 g/minute), medium (e.g., about 1 g/minute) and low (e.g., about 0.9 g/minute) rates. Three LED's 410 can selectively illuminate to indicate a selected fluid delivery level. As an alternative or in addition, an LCD display can be included to convey a fluid delivery level and/or can be used to display other information such as level of fluid in the oral care device 12 and/or status of battery charge.

As mentioned above, the controller 400 can be programmed as desired. Preferably, the controller 400 is programmed to adjust a paste delivery level subsequent to initiation of the motor 34. In some embodiments, the controller is programmed such that a relatively large bolus of fluid is delivered soon after motor 34 is initiated, e.g., to have enough paste to begin brushing, and then the level of paste delivery is decreased, e.g., to a lower delivery level throughout the remaining portion of the brushing cycle. The level of paste delivery may be decreased, for example, by intermittent bursts of fluid and/or by slower rates of fluid delivery. As an example, the controller may be programmed to provide three delivery settings, low, medium and high. In one embodiment, at the low delivery setting, the controller is programmed to deliver a bolus by activating the motor 34 for about seven seconds. After about seven seconds, the controller intermittently activates the motor 34 for about 0.75 seconds and deactivates motor 34 for about 2.4 seconds (i.e., cycles the motor on and off at these intervals). In the same embodiment, at the medium delivery setting, the controller is programmed to deliver a bolus by activating the motor 34 for about seven seconds, and then to cycle the motor on for about 0.75 seconds and off for about 1.63 seconds. At the high delivery setting, the controller is programmed to deliver a bolus by activating the motor 34 for about seven seconds and then to cycle the motor on for about 0.75 seconds and off for about 1.2 seconds. Depending on the desired programming of the controller 400, more or fewer user interface controls can be used to initiate various functions.

Docking Station

When not in use, oral care device 12 can be coupled with docking station 14. Docking station 14 can be connected to an electrical outlet (not shown) or other suitable power supply.

Figure 23B:
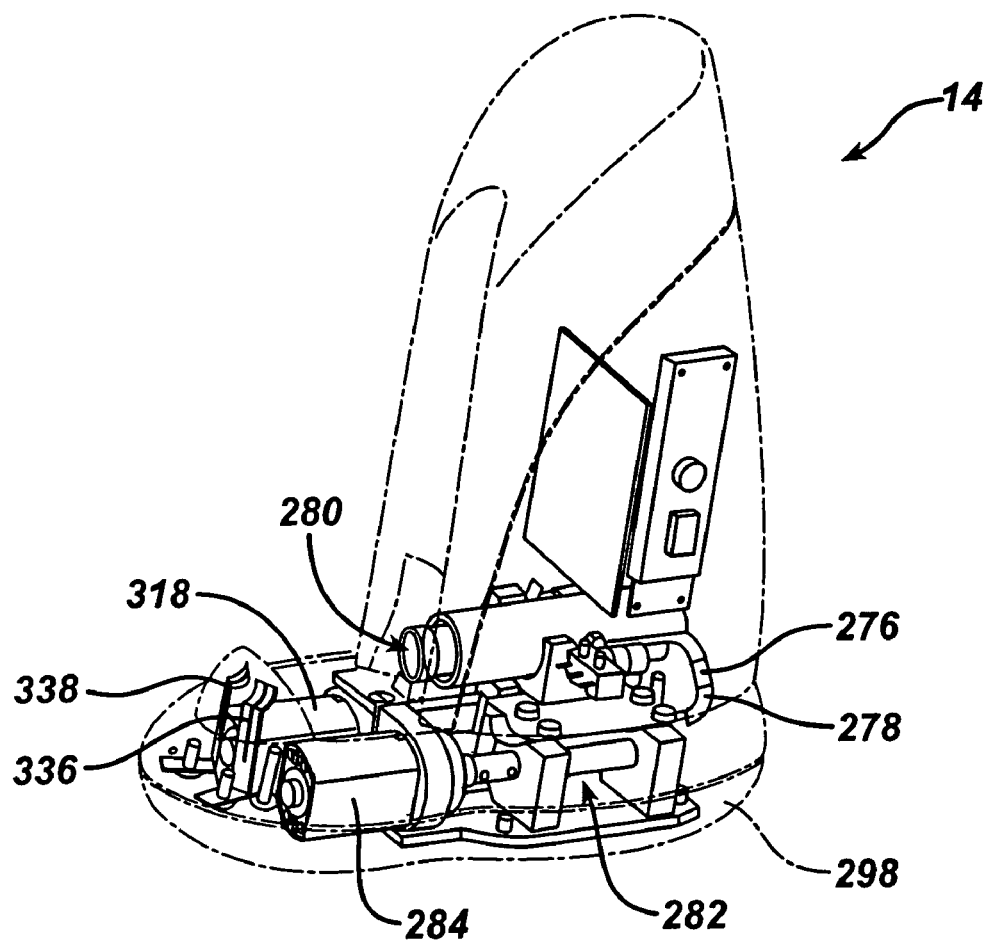
FIG. 23B is a transparent side perspective view of the docking station of FIG. 23A.

Referring to FIGS. 23A and 23B, docking station 14 is formed to hold oral care device 12 within the receiving portion 273 in an upright position. The receiving portion 273 is formed between a vertical recess 295 formed in housing 291 and housing extension 297 extending from base 293. The recess 295 is contoured to receive a portion of oral care device 12. The docking station 14 includes a reactive device, e.g., a sensor (not shown) that detects an input upon receipt of the oral care device by the docking station and, in response to this input, sends a signal to a controller, the details of which will be described in greater detail below.

Referring now to FIG. 23B, the docking station 14 includes a fluid reservoir 274 (see FIGS. 24 and 25) that is coupled with a tube 276 that forms a portion of a fluid passageway 278 extending from the fluid reservoir 274 to outlet 280. In some embodiments, as shown by FIG. 24, the fluid reservoir 274 is formed as an integral part of a separable, replaceable portion 301 of the docking station 14. In other embodiments, illustrated by FIG. 25, a replaceable pouch 303 forms the fluid reservoir. In this case, the upper portion 301 of the docking station is removable, to allow the consumer to easily remove pouch 303 when its contents are exhausted, or when the user wishes to use a different product, and insert a replacement pouch.

Figure 26A:
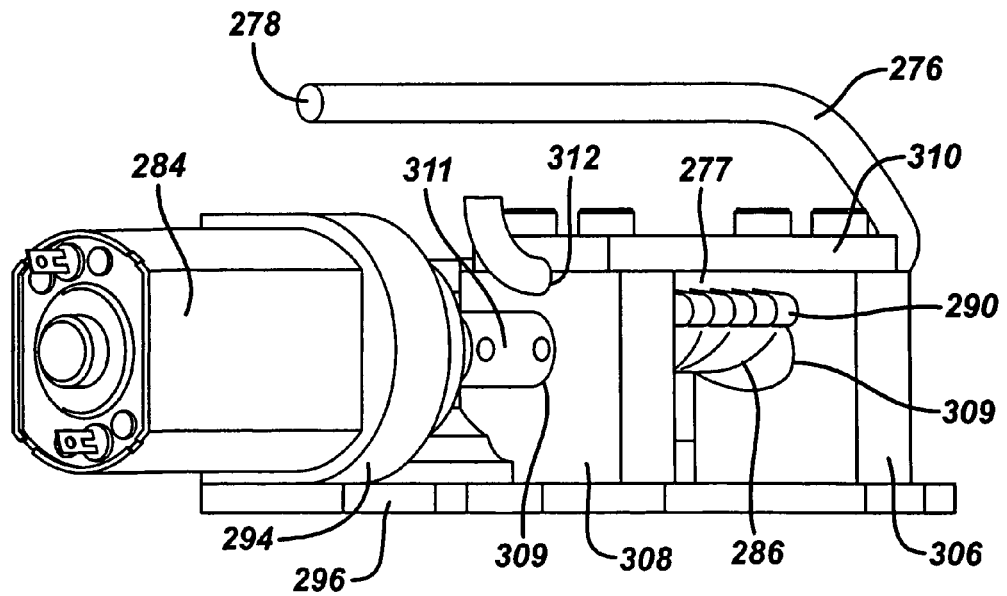
FIGS. 26A and 26B are side perspective views of a pump assembly embodiment.

Referring to FIG. 23B, to move fluid along the fluid passageway, the docking station includes a reversible pump assembly 282. As can be seen more clearly in FIGS. 26A and 26B, the pump assembly 282 is similar to the pump assembly depicted by FIGS. 4A and 4B in that it includes a motor 284, a screw 286 having an advancing spiral of enlarged dimension (see FIG. 26A), and an array of interconnected fingers 290 positioned to sequentially compress a compressible region 277 of the tube 276. In some embodiments, the motor 284, screw 286 including spiral and fingers 290 are of a construction substantially identical to the constructions described above. Other pump assemblies are also contemplated for moving fluid, particulate and/or powder along the passageway, such as a diaphragm pump, piston pump, compressed gas, gear pump, etc.

Figure 26B:
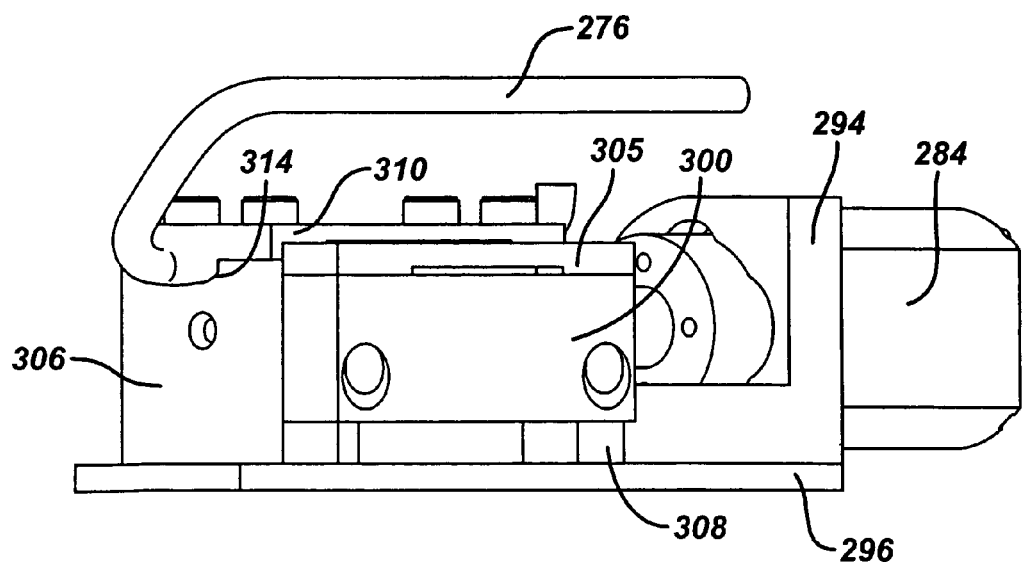

The motor 284 is mounted, using a bracket 294, on a support plate 296 that is secured to a floor 298 (see FIG. 23B) of the base station 14. The fingers 290 are secured along their base (see, for example, element 53 of FIG. 5A) to a plate 305 that is secured to a support member 300, which is mounted to side surfaces of pair of guide plates 306 and 308 (FIG. 26B). Mounted in this manner, the fingers 290 form a series of cantilevered projections positioned adjacent the tube 276. The guide plates 306, 308 are each mounted at their lower surfaces to the support plate 296. Guide plate 308 includes an aperture 309 sized to receive a coupling member 311 that connects the output from the gearbox to the screw 286 and guide plate 306 includes an aperture 309 that receives the screw 286.

Referring again to FIGS. 26A and 26B, a positioning plate 310 is provided to position the fluid-carrying tube 276 so that the compressible region 292 is adjacent the fingers 290. The positioning plate 310 is mounted to an upper surface of the plates 306, 308, and includes openings, defined by the lower surface of the positioning plate 310 and recesses 312 and 314 in the upper surfaces of each of the guide plates 306, 308, through which the tube 276 passes. Because the tube 276 is positioned and held in place by these openings, when the fingers 290 are displaced they compress the tube 276 in the compressible region 292 progressively along its length in a series of multiple compression events to force fluid along the fluid path.

Generally, motor 284 can be selected as desired. A suitable motor is a FF130SH, available from Mabuchi. The screw 286, the fingers 290 and the displacement sequence can be identical to those described above with reference to FIGS. 7A-7E.

Figure 27A:
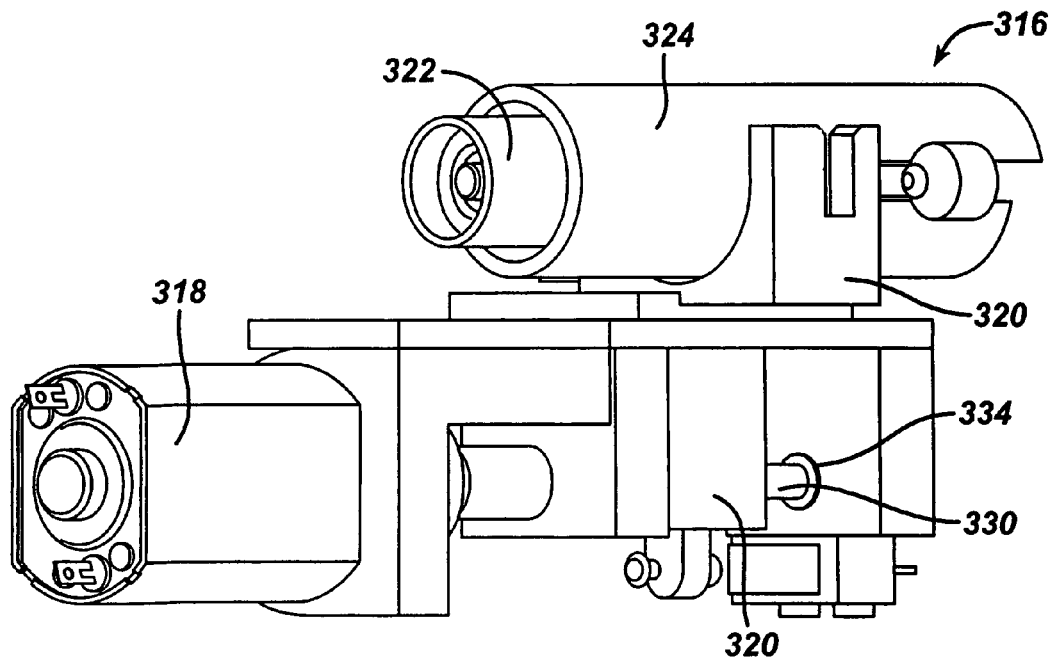
FIGS. 27A and 27B are side perspective views of a valve actuation assembly.
Figure 27B:
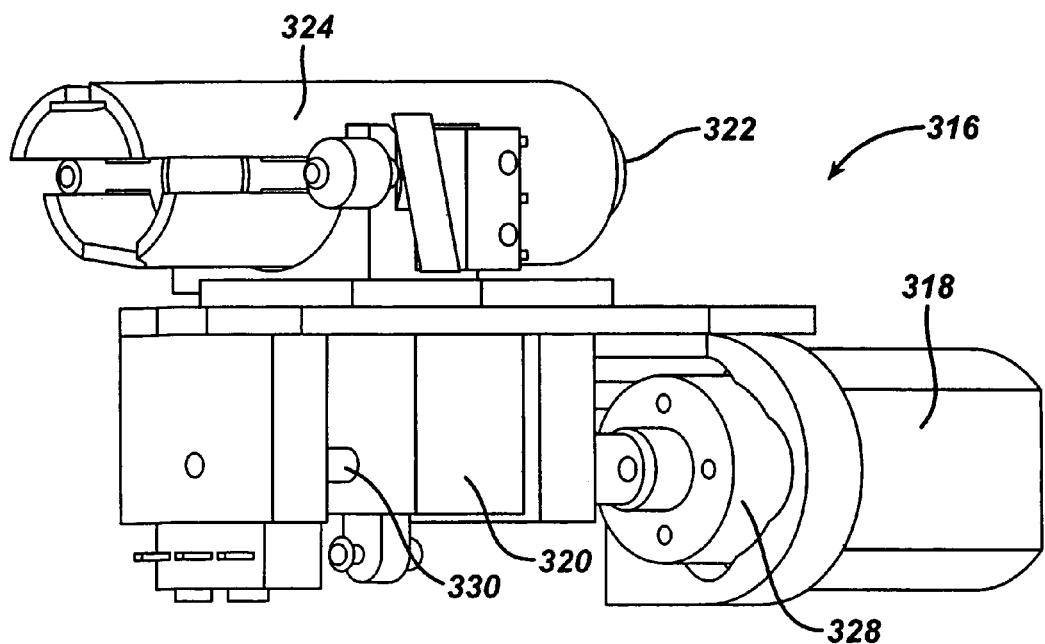

Downstream of the pump assembly 282, tube 276 is connected to a drive assembly 316 (FIG. 27A) that is used to extend and retract valve 322 to engage and disengage, respectively, valve 200 of the oral care device 12. Although valve 322 is depicted, any suitable coupling can be used that is constructed to couple with the oral care device and provide communication between the fluid reservoir 274 and the oral care device. The drive assembly 316 includes a motor 318 capable of moving a sled 320 that is connected to the valve 322, which is fluidly connected (e.g., using a barbed fitting) to the tube 276. Referring now to FIGS. 27A and 27B, the valve 322 is slidably positioned within a fixed bushing 324. To move the sled 320 and associated valve 322, the motor 318 and an associated gear box 328 are connected to a lead screw 330, using a coupling which is threadably connected to the sled 320. As the motor 318 rotates the lead screw 330, the sled 320 is pulled or pushed toward or away from the motor 318, depending on the direction of rotation of the lead screw 330. The lead screw 330 is connected to a pair of bearings 334, which aid in positioning the lead screw 330. As noted above, valve 322 is positioned at outlet 280 to control the flow of fluid from the outlet 280, and is matable with valve 200 that controls fluid flow into the inlet 28 of the oral care device 12. As an alternative, in some embodiments, the valve can be mechanically actuated using other drive mechanisms, for example, a spring mechanism (e.g., by spring-loading the valve and releasing the valve using a button) and/or a lever that can cause the valve to extend and/or retract.

Referring back to FIG. 23B, a pair of leads 336, 338 are exposed within the receiving portion 273 of the docking station 14. Leads 336, 338, are positioned to contact a pair of contacts 340, 342 (FIG. 2A) on the oral care device 12 when the oral care device 12 is placed within the receiving portion 173. This contact will electrically couple the oral care device 12 and the docking station 14, so that the power source to which the docking station is connected can recharge the rechargeable batteries within the oral care device. Contacts 340, 342 are electrically connected with the rechargeable batteries, allowing power to flow from the docking station to the batteries.

Figure 28:
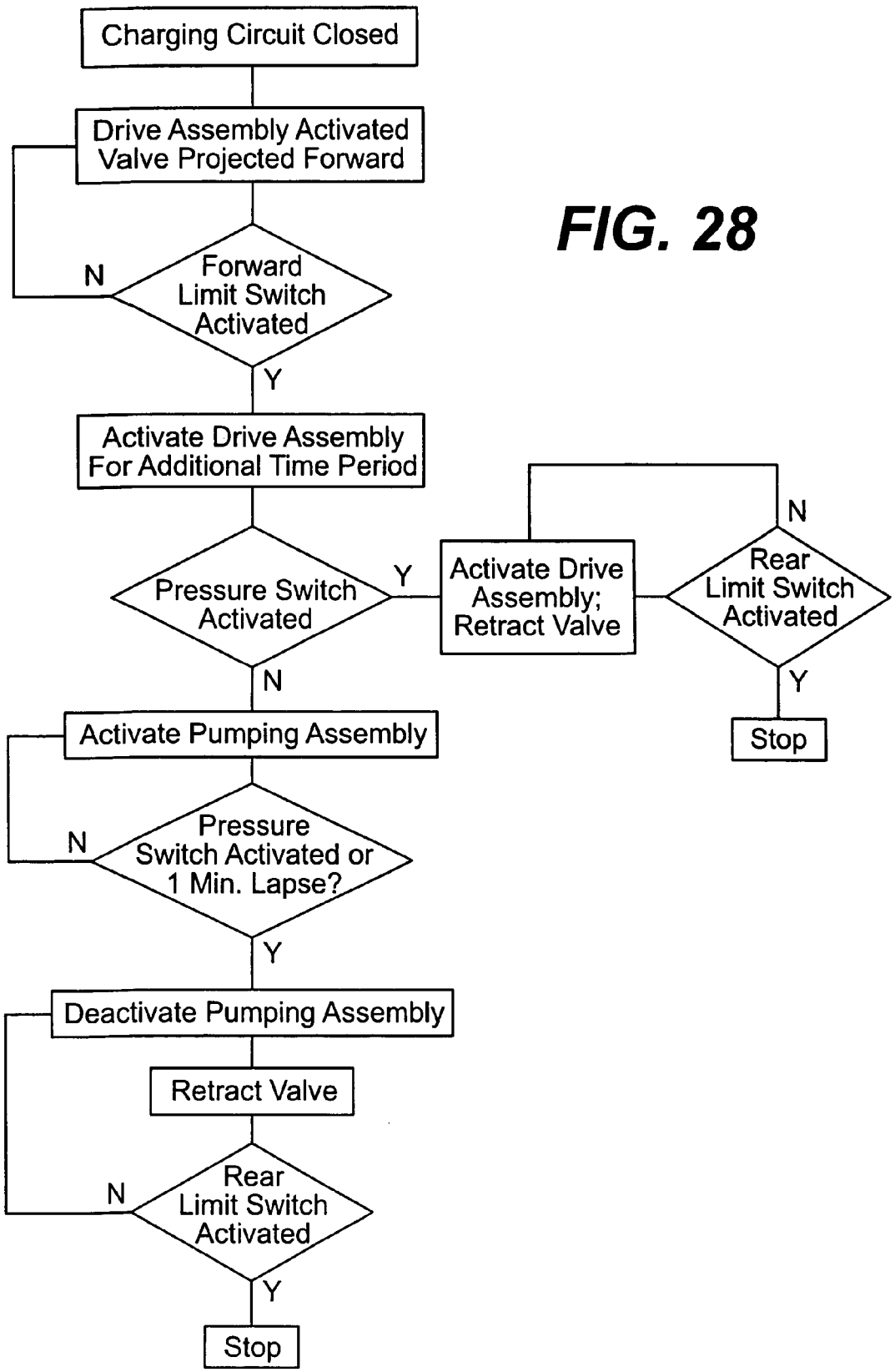
FIG. 28 is a diagram of an oral care system control embodiment.

With reference to FIG. 28, by placing the oral care device 12 within receiving portion 273 such that contacts 340, 342 mate with leads 336, 338 a charging circuit is closed, which is recognized by the controller. When the charging circuit is closed, the rechargeable batteries 44 begin to charge. The charging circuit can include an inductive component for charging the batteries 44 inductively. In some embodiments, the oral care device is electrically connected to the docking station mechanically or by using a signal from a magnetic field, electrical field or radio frequency identification (RFID), as examples. As the charging process begins, the motor 318 of the drive assembly 316 is activated and the valve 322 projects forward to mate with the valve 200 (FIG. 2B) in the handle 24. A limit switch (not shown) determines the end of travel of the valve 322. Once the limit switch is actuated, the valve 322 can be projected forward by the drive assembly 316 for an additional selected period of time (e.g., about two seconds), which can ensure that valves 200 and 322 are seated. During the selected period of time, the valve 322 may or may not travel forward. The selected period of time for travel is primarily used to help ensure that that the valves 322 and 200 are mated.

Upon activation of the limit switch and expiration of the selected period of time, the controller is programmed to determine if a pressure switch (not shown) has been actuated. The pressure switch is plumbed into the passageway 278 (or, in some embodiments, into passageway 40 of oral care device 12) and will actuate when pressure in the passageway exceeds a preselected threshold, e.g., eight psi (preferably between six and ten psi). If this threshold is exceeded, this indicates that the fluid passageway 40 in the oral care device is full. Once the valves are mated, if the fluid path in the oral care device is not already full (i.e., if the pressure switch is not activated) then the pumping assembly 282 is activated and pumps fluid from the reservoir 274 in the docking station to the fluid passageway 40 within component 154 of the oral care device 12, refilling the supply of fluid within the fluid path of the oral care device 12.

If, however, the controller detects that the pressure switch is actuated prior to activating the pumping assembly 282 (i.e., if the fluid passageway of the oral care device is already full when the oral care device is placed on the docking station), the motor 284 is not activated and the valve 322 is retracted until a rear limit switch (not shown) is actuated.

During a refill operation, when pressure in the passageway reaches the threshold the pressure switch is actuated and the controller signals the motor 284 to deactivate to discontinue pumping of fluid and signals the drive assembly 316 to retract the valve 322 to its starting, closed position. As an alternative, in some embodiments, upon actuation of the pressure switch, the controller opens a bypass valve that directs fluid back to the fluid reservoir. A similar operation can also be accomplished, for example, by use of a pressure relief valve, which does not require a pressure switch. The rear limit switch actuates when the valve 322 is retracted to its starting position.

As explained above, the fluid passageway 40 is filled until pressure within the passageway reaches the preselected threshold, indicating that the component 154 has reached a predetermined capacity. As an over-spill prevention measure, the controller can deactivate motor 284 after a selected time period (e.g., one minute, preferably between 30 seconds and 2 minutes) has lapsed, regardless of whether the pressure switch has actuated. This can prevent the docking station 14 from emptying the fluid reservoir 274 (e.g., in the event of a valve mating problem or a broken component 154). When the valves 322 and 200 are mated (FIG. 19), the oral care device 12 cannot be removed from receiving portion 273. The mated valves lock the oral care device 12 to the docking station 14, e.g., to maintain a fluid connection between the oral care device 12 and the docking station 14.

In some embodiments, only one motor housed within the docking station 14 is used to drive the valve 322 and to pump fluid along the fluid passageway 278. In these cases, a clutch can be used to selectively engage the motor with the drive assembly and the pump assembly. In some cases, the pump assembly 38 within the oral care device 12 is used to pull fluid from the fluid reservoir of the docking station to refill the passageway 60 within the cartridge component 154. This can render unnecessary the pumping assembly 282 within the docking station 14.

Figure 29:
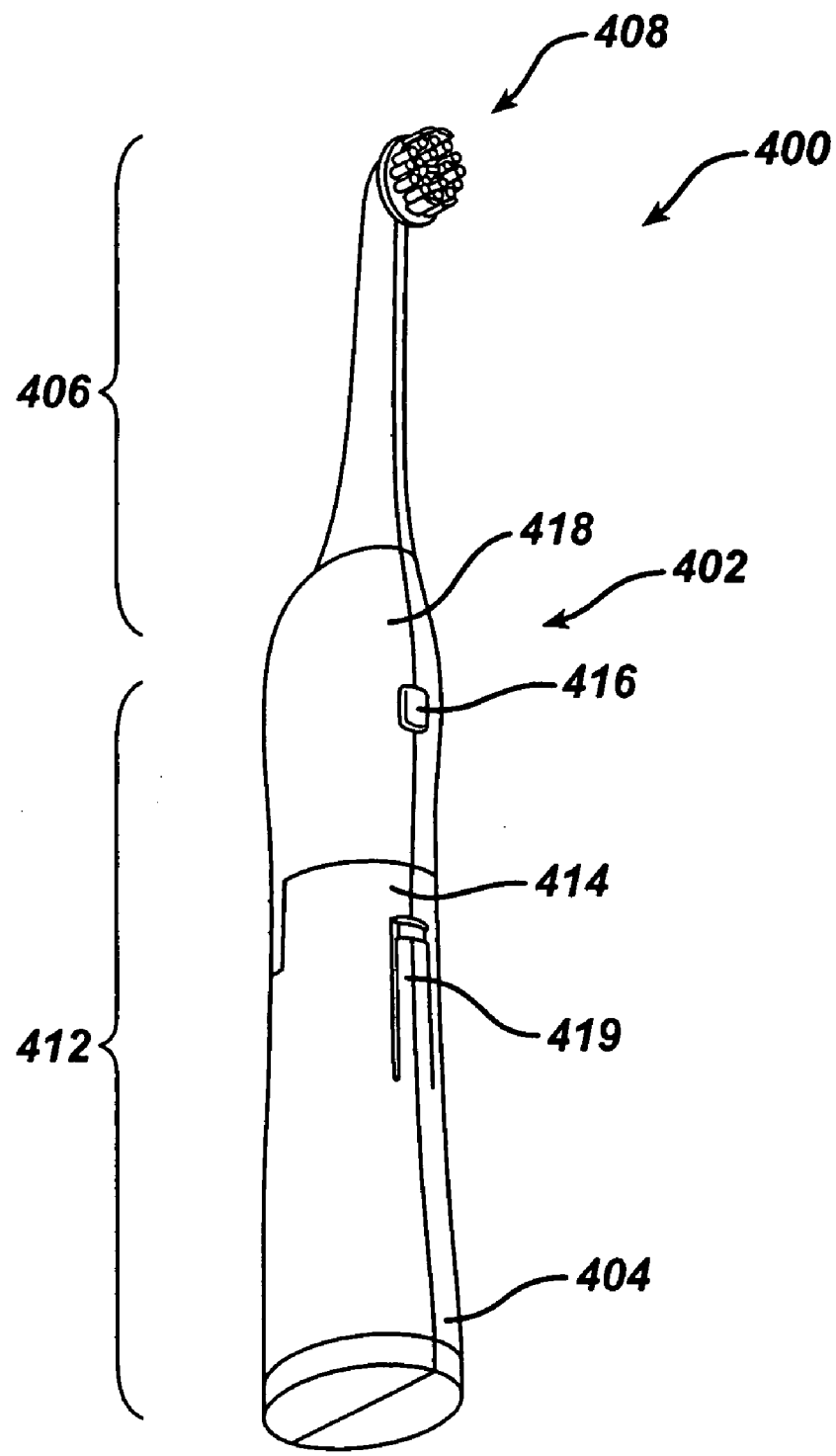
FIG. 29 is a perspective side view of another embodiment of an oral care device.

Referring now to FIG. 29, an alternative oral care device 400 is shown that includes a separable bi-component housing 402 with a separable and replaceable cartridge 404. Similar to the oral care device 12 described above, oral care device 400 is a power toothbrush having a motorized head and is designed to discharge a fluid, such as a dentifrice or mouthwash or a combination of various fluids, during the brushing cycle. As will be discussed in detail below, the oral care device 400 includes a body component 418 and the separable cartridge component 404 that includes both a fluid reservoir (that can be refillable and/or disposable) and batteries (that can be rechargeable or disposable) or other power source. The body and cartridge components are secured together by snap latch 419. In some embodiments, the entire cartridge component 404 is disposable.

As assembled, the oral care device 400 includes a distal portion 406 at which a movable head 408 and neck 410 is located and a proximal portion 412 at which a handle 414 is located. The head 408 is sized to fit within a user's mouth for brushing, while the handle 414 is graspable by a user and facilitates manipulation of the head 408 during use. The oral care device 400 includes a user interface 416 in the form of an on/off button.

As noted above, the cartridge component 404 is separable from the body component 418 (see FIG. 31A). As shown in FIGS. 30A and 30B, the cartridge component 404 is a removable, replaceable cartridge capable of carrying a fluid (e.g., dentifrice, mouthwash, water) within a fluid reservoir 405 (e.g., a rigid container or a flexible pouch). The body component 418 also includes a power source 420 (see FIG. 30B). By providing the cartridge component 404 with a power source (e.g., one or more batteries) and a fluid reservoir, the need for a docking station capable of both refilling and recharging the cartridge component, can be eliminated. In some embodiments, a refilling station, a recharging station and/or a combination of a refilling and recharging station is provided for refilling the cartridge component 404 and/or recharging the power source 420. In other embodiments, a simple docking station that neither refills nor recharges may be provided as a holder for the oral care device.

Referring now to FIGS. 31A and 31B, the body component 418 includes the movable head 408, and, housed internally within the body component 418, a pair of motors 34 and 36. Motor 34 drives a pumping assembly 438 that is used to transfer a fluid along a fluid passageway 40 toward the head 408 of the oral care device 400. In some embodiments, motor 34 is reversible and can move fluid in an opposite direction, toward the proximal portion of the oral care device 400 (e.g., to reduce or, in some cases, even eliminate any leaking of fluid from the head that may occur due to pressure build-up within the passageway). Motor 36 drives a drive shaft 442, which in turn moves (e.g., rotates) the head 408. When the cartridge component 404 is connected to the body component 418 (as shown in FIG. 29), the power source 420 is electrically coupled to the motors 34, 36 for providing power thereto.

The head drive assembly is similar to the head drive assembly of the oral care device 12, discussed above, in that the drive shaft 42 is connected to the rotatable head 408 using an offset design that facilitates placement of a fluid outlet at the head 408 and a tube 422 forming the fluid passageway 40 within the neck 410 of the housing 402. The drive shaft 42 is moved by use of a cam and follower system that translates rotational output of the motor 36 into linear motion used to drive the drive shaft 42 backward and forward. In some embodiments, the head drive assembly is substantially identical to that shown by FIGS. 10A-13 (and may include any alternatives) as those described above.

As can be seen by FIG. 31B, the pumping assembly 438 is similar to the pump assembly 38 depicted by FIGS. 4A and 4B in that it includes the motor 34, a screw 48 having an advancing spiral 50 of enlarged dimension, an array of interconnected fingers 56 and a tube 422 having a compressible region 58 that forms at least a portion of fluid passageway 40. In some embodiments, the motor 34, screw 48 including spiral 50, tube 422 and fingers 56 are of substantially identical construction to the constructions described above, and may include any of the alternatives discussed above.

Each of the housing components 404 and 418 contains a portion of fluid passageway 40. In order to reduce or, in some cases, to even prevent fluid leakage from the fluid passageway 40 when components 404 and 408 are separated, valves 160 and 162 having a "normally closed" configuration are provided at the proximal end of the body component 418 and at the distal end of the cartridge component 404, respectively. (Suitable valves having a "normally closed" configuration are shown, for example, in FIGS. 18C and 19C and discussed above. Other types of valves may be used, such as that described with reference to FIGS. 40A and 40B below.) As discussed above with respect to the valves shown in FIGS. 18C-19C, valves 160 and 162 close passageway 40 when the body component 418 and the cartridge component 404 are separated, and allow fluid flow through passageway 40 when the components are joined.

Other Embodiments

Figure 32:
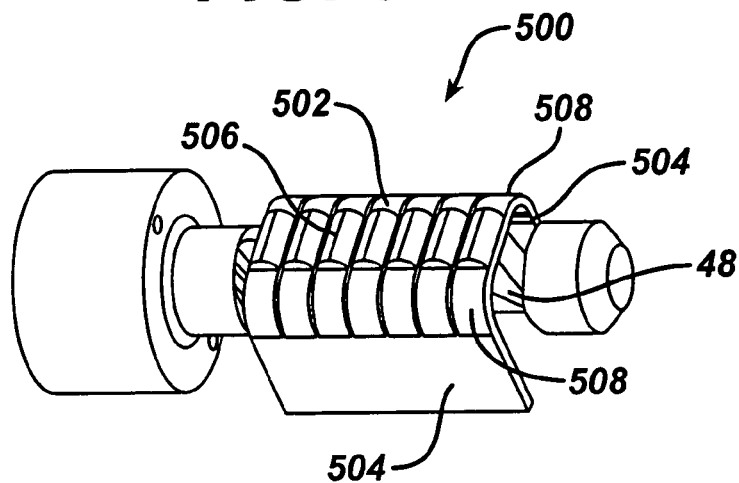
FIGS. 32, 33 and 34 are perspective views of alternative compression member array embodiments.
Figure 33:
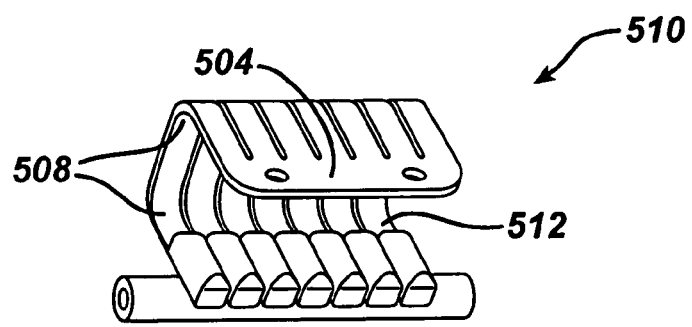
Figure 34:
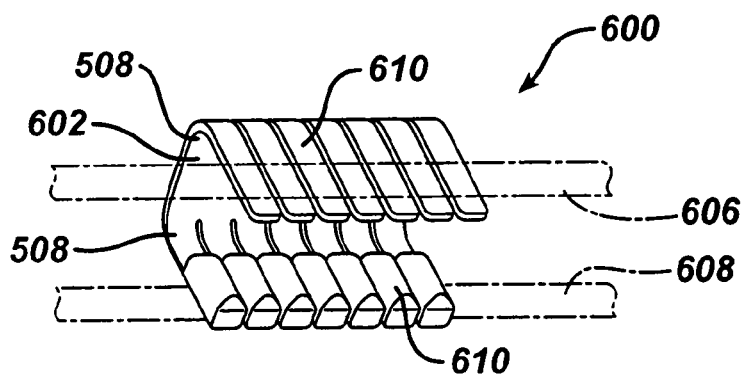

Referring now to FIGS. 32, 33 and 34, three alternative compression element arrays are shown that include compression elements having multiple bends 508, e.g., to facilitate placement of the compression element arrays within the oral care device. The curvature can be 180 degrees, as shown, but other configurations may be used, such as a 90 degree curvature. Referring to FIG. 32, compression element array 500 includes multiple, interconnected compression elements 502. Each of the compression elements 502 is supported at both ends by bases 504, each of the bases 504 also interconnecting the elements 502 of the array. The compression elements 502 are formed to buckle upon application of a force, such as that applied by screw 48. As the elements 502 buckle, an associated compression surface 506 is displaced, which, in turn, can displace, for example, an adjacent compressible tube. Referring to FIG. 33, another compression array 510 includes multiple, interconnected compression elements 512 that are supported at only one end by a base 504.

Referring now to FIG. 34, compression array 600 is capable of compressing a pair of compressible fluid conduits 602 and 604 to pump fluid along a pair of associated fluid passageways 606 and 608 (shown by dashed lines). The compression elements 610 extend from a common base 612 that also interconnects each compression element 610 of the two arrays. An advantage of the embodiment shown is that a single shaft with spiral can be utilized to displace both arrays of compression elements by placing the shaft with spiral (not shown) between the two arrays of compression elements 610. In some embodiments, multiple, separate arrays of compression elements can be used, such as that shown by FIG. 5B, along with multiple shafts with spirals, such as that shown by FIG. 6A, to pump fluid along multiple, respective passageways.

Figure 35A:
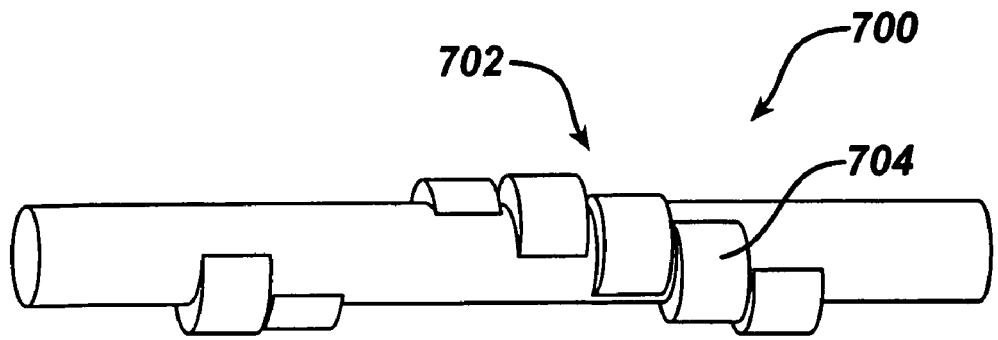
FIGS. 35A and 35B show an alternative screw embodiment.
Figure 35B:
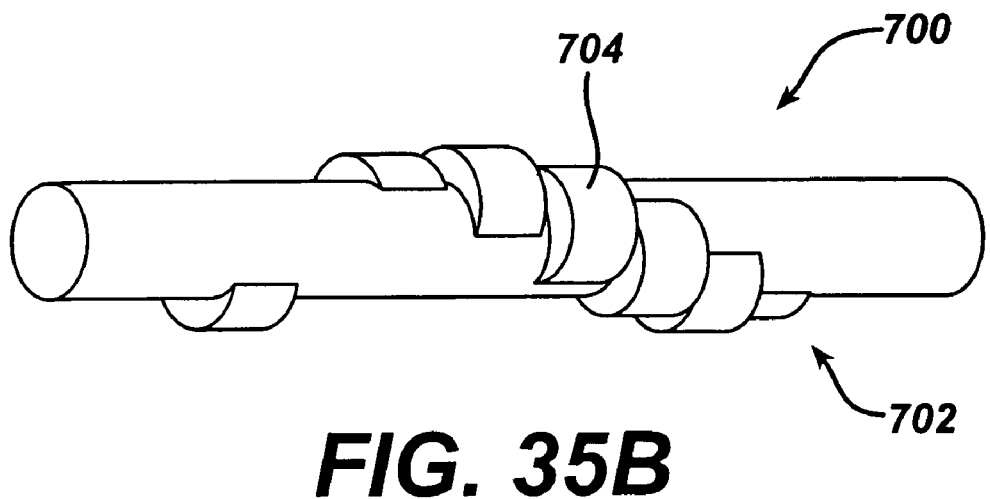

An alternative screw embodiment 700 is shown by FIGS. 35A and 35B where spiral 702 is formed of multiple, discontinuous projections 704. The projections 704 are arranged and formed to displace an array of compression elements, e.g., as described above with reference to FIGS. 7A-7E.

Figure 36A:
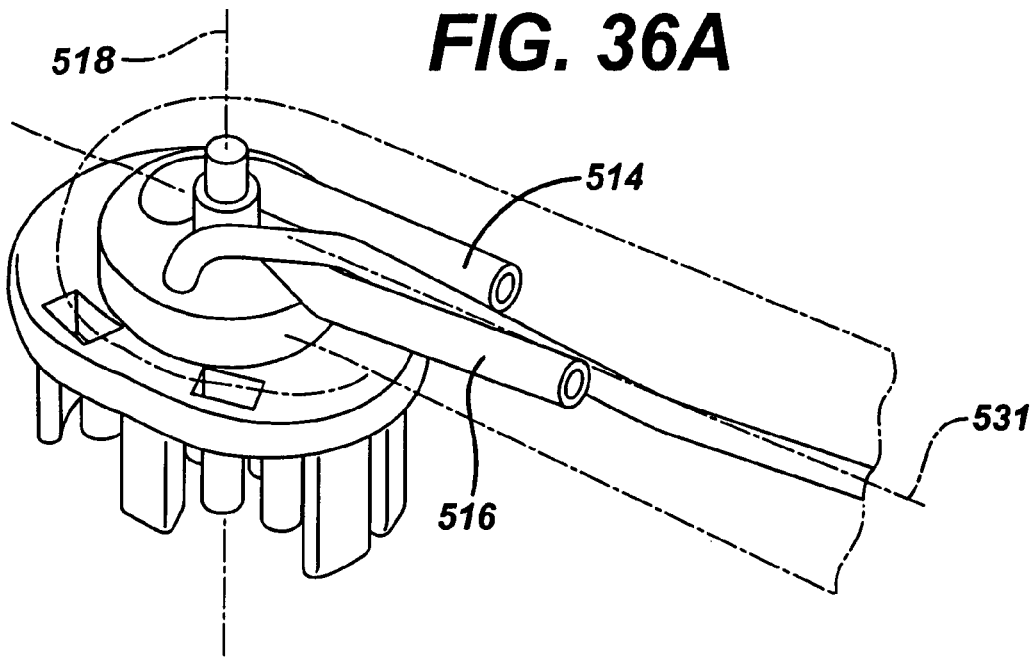
FIGS. 36A and 36B are rear and front views, respectively, of the head and neck of another oral care device embodiment with the neck shown as transparent.
Figure 36B:
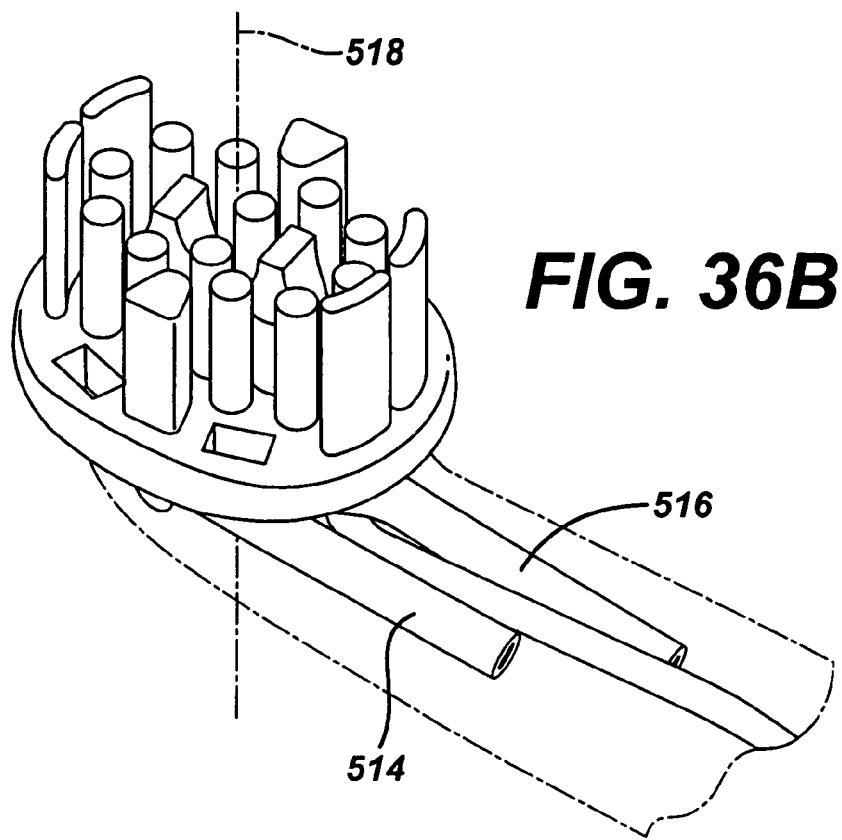
Figure 37:
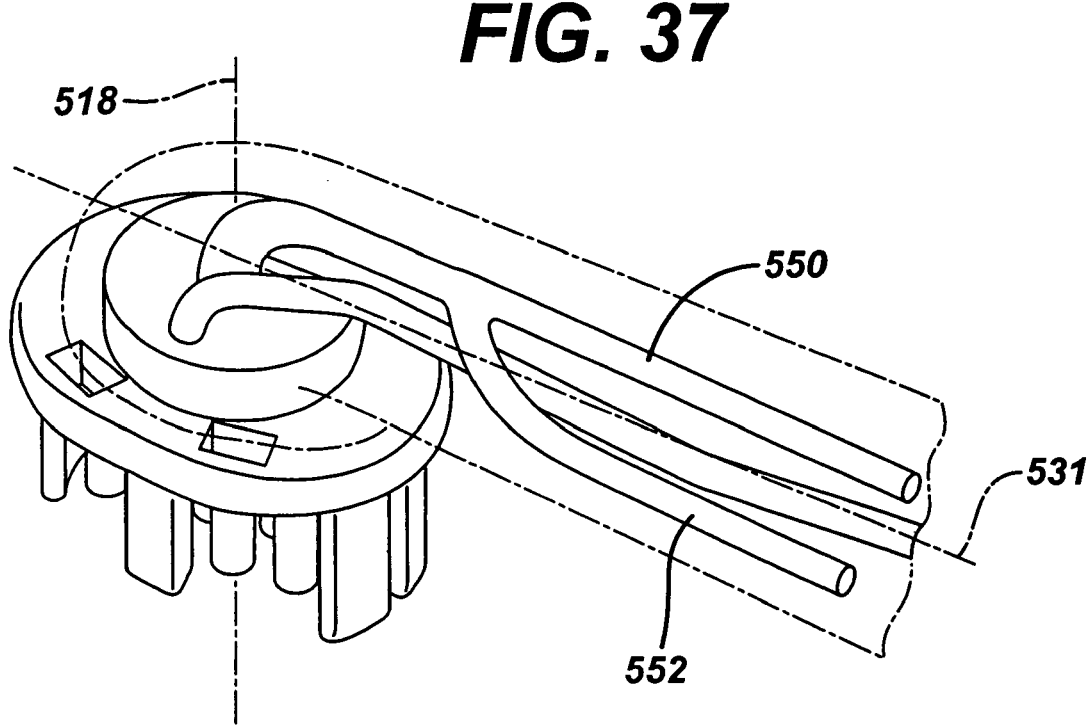
FIG. 37 is a rear view of the head and neck of another oral care device embodiment with the neck shown as transparent.

As indicated above, the oral care device can include more than one fluid passageway. Referring to FIGS. 36A and 36B, the oral care device includes a pair of tubes 514 and 516 to direct two fluid streams (e.g., of the same or of differing fluids) within the oral care device. As shown, each of the tubes 514 and 516 is connected to the head at a location offset from a longitudinal axis 531 perpendicular to an axis of rotation 518 of the movable head 408. In some embodiments, one of the tubes 514, 516 may be connected to the head at the axis of rotation 518 and the other connected at a location offset from the axis of rotation 518. Referring to FIG. 37, a variation is shown where tubes 550 and 552 are fluidly connected to each other downstream of the pumping assembly and upstream of a fluid outlet at the head. This embodiment may be advantageous where it is desirable to mix fluids within the passageways at a time just prior to delivery to a brushing surface.

Figure 38:
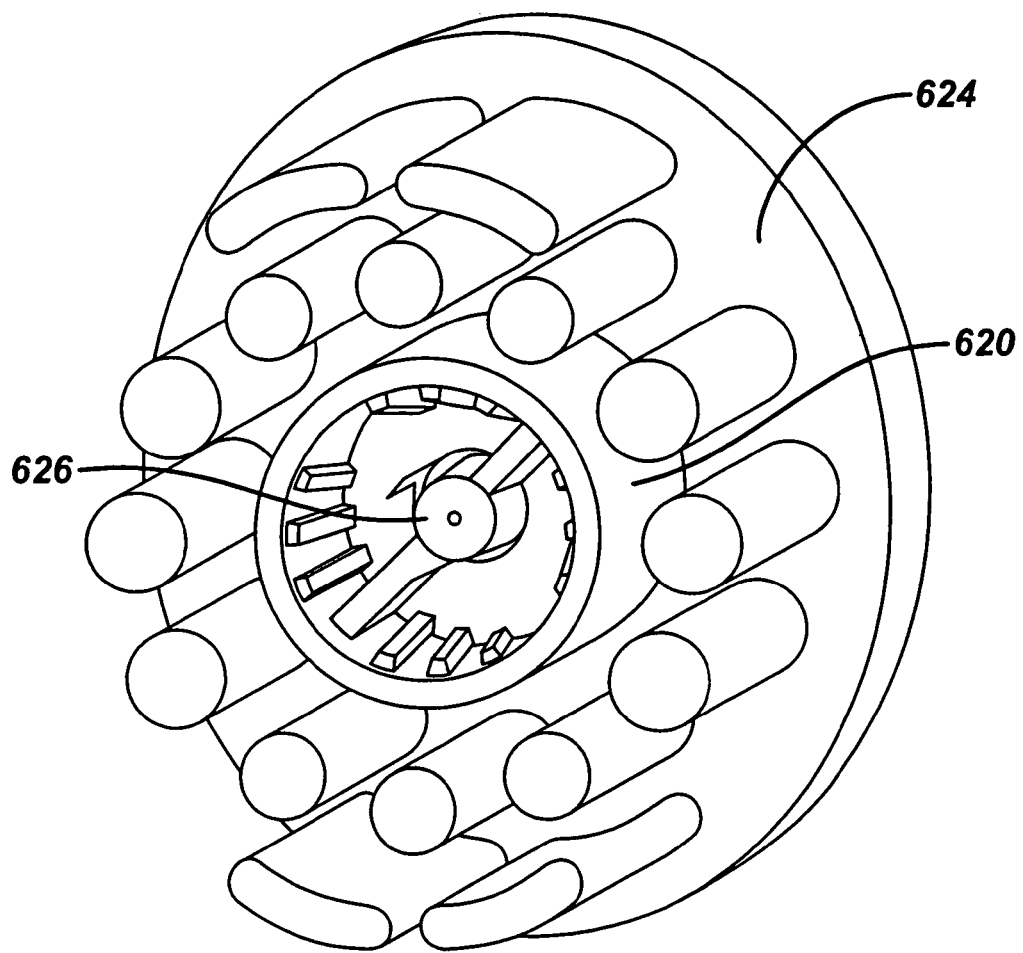
FIGS. 38 and 39 illustrate alternative head embodiments.
Figure 39:
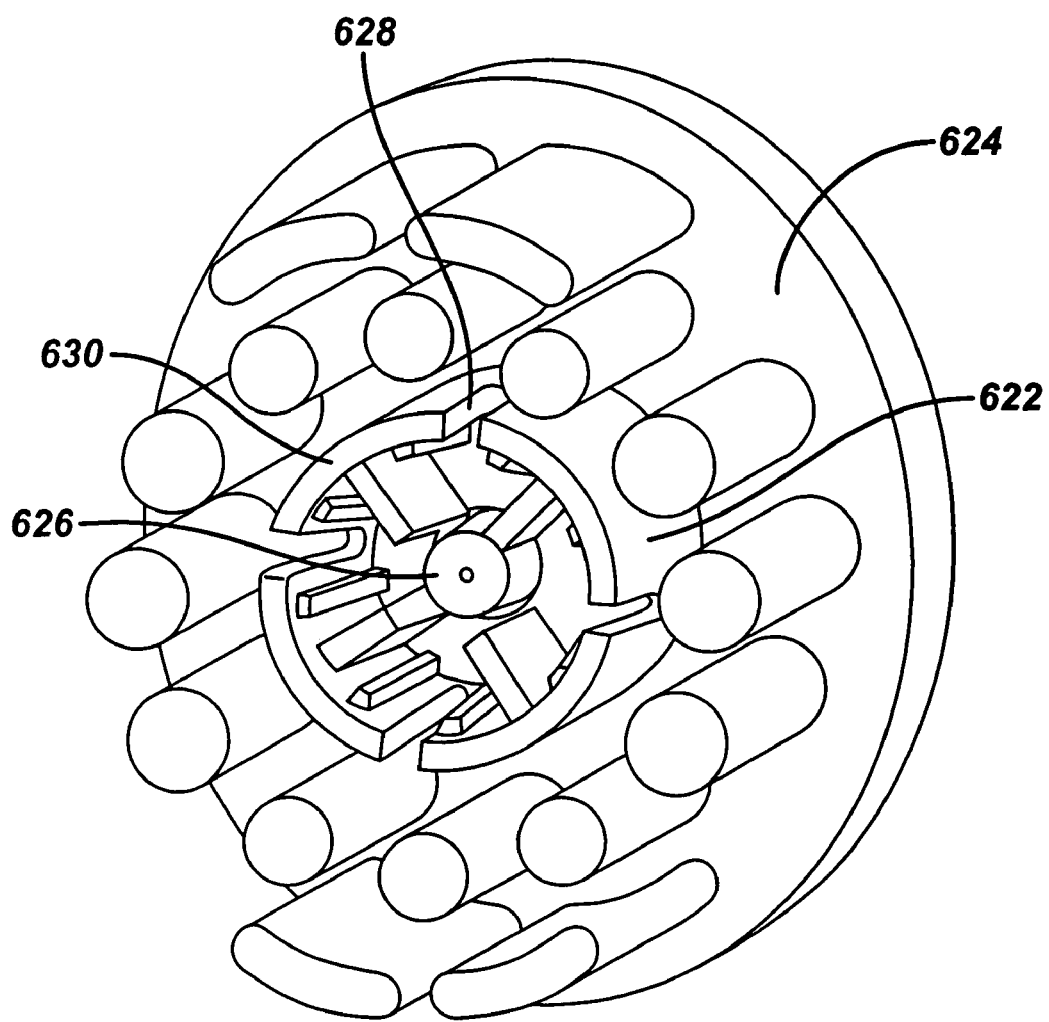

Referring to FIGS. 38 and 39, the head may include a prophy cup 620, 622 (or other guiding member, such as a pick). As shown by FIGS. 38 and 39, the prophy cups 620 and 622 extend from base 624 and around nozzle 626. In FIG. 39, the prophy cup 622 is castellated and includes openings 628 positioned along a ridge 630 of the prophy cup, which can aid in cleaning.

FIGS. 40A and 40B illustrate an alternative valve assembly 800 embodiment, e.g., to replace valves 160 and 162 which can provide communication between the head component 152 and the cartridge component 154 (see, e.g., FIGS. 18B and 19B) and/or to replace the valves 200 and 322 which can provide communication between the cartridge component 154 and the docking station 14 (see, e.g., FIG. 21). Valve assembly 800 includes a fitment 802 having a passageway 804 extending therethrough. Positioned within the passageway 804 is a spring-biased ball 806 that is biased by a spring 808 toward a sealing ring 810 extending into and coaxial with the passageway 804. Referring to FIG. 40A, valve assembly 800 is shown in a closed position with the ball 806 biased against the sealing ring 810 sealing the passageway 804. Referring now to FIG. 40B, valve assembly 800 is shown in the open position with the ball 806 forced apart from the sealing ring 810 by a conduit 812 that is received by the fitment 802. The conduit 812 includes multiple ports 814 extending through a sidewall 816 of the conduit 812. The ports 814 allow fluid to pass therethrough and into the passageway 804 when an end 818 the conduit 812 abuts ball 806. In the open position, fluid, particulate or any other suitable material can flow past the ball 806 during use toward and/or, in some embodiments, away from, e.g., the head 20 of oral care device 10.

Referring now to FIGS. 41 and 42, fluid reservoirs suitable for use with certain oral care device embodiments, e.g., oral care devices including one or more features described above, are in the form of refillable pouches 850 and 900, respectively. As shown, pouches 850 and 900 are refillable. In some cases, the pouches are replaceable and can be disposable, e.g., when the pouch is emptied. Pouch 850 and 900 includes a pair of sidewalls 852, 854 that are joined along opposite longitudinal side edges 856, 858 by respective seams 860 and 862. In some embodiments, the side edges can be joined along one longitudinal side edge by a seam and along an opposite longitudinal side edge by a fold. The sidewalls 852, 854 are also joined along a top edge 864 and a bottom edge 866 by seams 868, 870. The sidewalls 852, 854 form a pouch body 872 having a volume formed between the sidewalls.

Extending into the pouch body 872 and having an end 882 (FIG. 43) disposed between the sidewalls 852, 854 at the top edge 864 is a fitment 874. Fitment 874 provides communication between the pouch body 872 and the fluid conduit extending through the oral care device. In some embodiments, referring to FIG. 44, the fitment 880 extends through an opening formed in sidewall 852. Referring again to FIGS. 41 and 42, connected to the fitment 874 is valve 200 having a normally closed construction, as described above.

Figure 43:
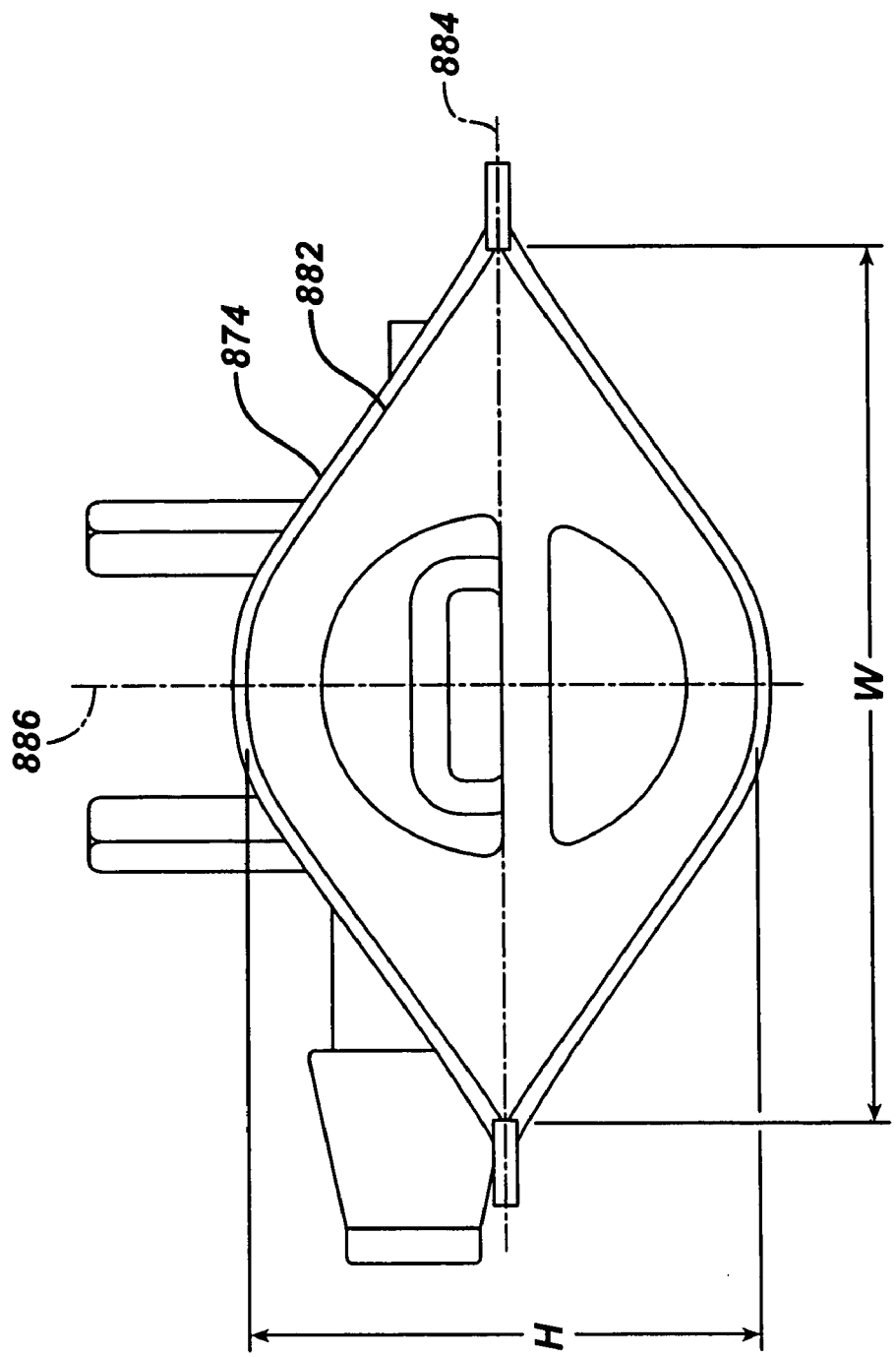
FIG. 43 is an end view of a fitment of FIGS. 41 and 42.
Figure 44:
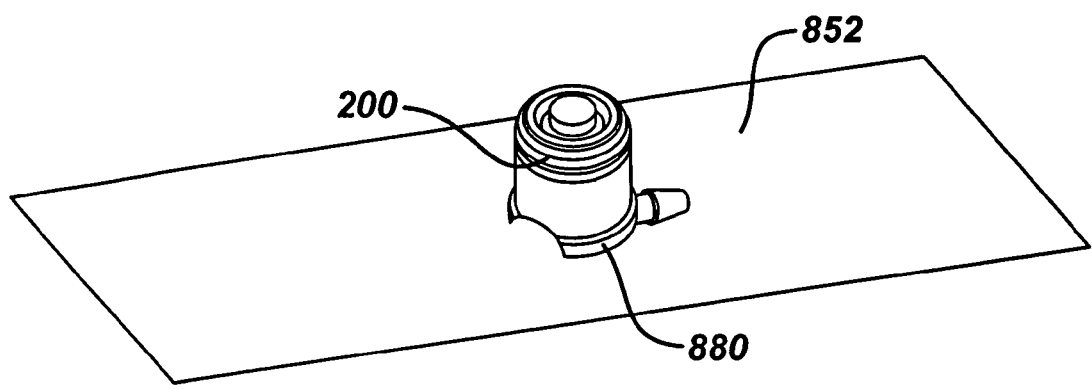

Referring now to FIG. 43, the end 882 of the fitment 874 has a width W that is greater than a height H of the fitment, W and H being measured along perpendicular major and minor axes 884, 886 (each axis shown in phantom), respectively (i.e., a height to width aspect ratio of the fitment 874 is less than one, preferably at most about 0.65, such as about 0.55).

The pouch including fitment is constructed such that the volume of the pouch body increases from an original, unfilled volume as the pouch is filled with content, the volume decreasing as the pouch is emptied. When the pouch is substantially emptied, such as at least about 95 percent empty, the volume of the pouch is substantially equivalent to the original, unfilled volume (e.g., the volume is within at least about 40 percent of the original, unfilled volume, preferably at least about 20 percent of the original unfilled volume, such as at least about 10 percent of the original unfilled volume), with shoulders 888 and 890 of the pouch collapsed substantially flat. This construction can allow the pouch to be emptied without significant material fatigue, e.g., allowing the pouch to be refilled and reused, and can facilitate use of stiffer materials for forming the sidewalls.

Pouches 850 and 900 can have a laminate structure that includes inner and outer layers that form the sidewalls 852, 854, or the sidewalls can be of unitary structure having only a single layer. In embodiments having multiple layers forming the sidewalls, the layers can be of differing materials, or each of the layers can be of the same material. To form the pouches 850 and 900, the pouch body can be formed of a single sheet of plastic film (or multiple sheets e.g., two sheets) of plastic film that is folded in half and sealed on the folded edge and the two open edges. The fitment is then inserted into the open edge and the edge is sealed with the fitment disposed between the two sidewalls. In some embodiments, as noted above, the folded edge may not be sealed. In some embodiments, the pouch body is rounded on one end and a continuous rounded seam seals the rounded end of the pouch body (not shown).

Suitable materials for forming the pouch body include acrylonitrile co-monomer, acrylonitrile-methyl acrylate copolymer (e.g., BAREX® resin), polyethylene, polypropylene, polyester, fluoropolymers, e.g., PCTFE or CTFE, polyethylene terephthalate or a combination thereof. The fitment can also be formed of any suitable material, such as acrylonitrile-methyl acrylate copolymer (e.g., BAREX® resin). The sidewalls (or at least a layer of the sidewalls) may comprise a laminate structure including an inner layer and an outer layer, the inner layer comprising a material having a flexural modulus of at most about 500,000 psi. In some embodiments, the sidewall (or at least a layer of the sidewall) is between about 25 and 100 microns thick.

A number of embodiments of the invention have been described. Nevertheless, it will be understood that various modifications may be made without departing from the spirit and scope of the invention. Accordingly, other embodiments are within the scope of the following claims.

What is claimed is:

1. An oral care device comprising:
    a head component including a head portion sized to fit within a user's mouth and a first fluid passageway for directing fluid to an outlet at the head portion;
    a replaceable and refillable cartridge releasably connected to the head component, the cartridge comprising a second fluid passageway in fluid communication with the first fluid passageway, wherein the cartridge is configured to be refillable while connected to the head component; and
    a first valve in fluid communication with the first fluid passageway and a second valve in fluid communication with the second fluid passageway, wherein the first valve and the second valve are configured to close the respective the first and the second fluid passageways when the head component and cartridge are separated, and are in fluid communication when the head component and the cartridge are mated together, the first and the second valves located at the end portions of the respective fluid passageway;
    wherein the second passageway includes a compressible region located on the interior of the device and configured to be compressed thereby facilitating a flow of a fluid therethrough.

2. The oral care device of claim 1, wherein the cartridge includes an inlet for refilling the cartridge and an outlet connected to the first fluid passageway, the inlet and the outlet being in communication with the second fluid passageway.

3. The oral care device of claim 1, wherein the first and the second valve include a sealing member configured to close the respective passageway when the head and cartridge components are disconnected.

4. The oral care device of claim 3, wherein the sealing member is configured to open the respective passageway when the head and cartridge are connected.

5. The oral care device of claim 3, wherein the sealing member closes the respective passageway to form a fluid-tight seal.

6. The oral care device of claim 3, wherein the sealing member is selected from a group consisting of a poppet and a ball.

7. The oral care device of claim 1, wherein the first and the second valve are of a normally closed construction, the first and second valve configured to open when the head and cartridge components are connected.

8. The oral care device of claim 7, wherein the first and the second valve are configured to mate with a fluid coupling when the head and cartridge components are connected.

9. The oral care device of claim 8, wherein the fluid coupling is configured to open the first and the second valve when the head and cartridge components are connected.

10. The oral care device of claim 8, wherein the fluid coupling comprises a fitment.

11. The oral care device of claim 1 further comprising a pumping assembly configured to pump fluid along at least one of the fluid passageways toward the outlet.

12. The oral care device of claim 11, wherein the pumping assembly is reversible and configured to pump fluid in a direction away from the fluid outlet.

13. The oral care device of claim 1 further comprising a body component releasably connected to at least one of the head component and the cartridge component.

* * * * *